(12) United States Patent
Takeguchi et al.

(10) Patent No.: US 9,153,033 B2
(45) Date of Patent: Oct. 6, 2015

(54) MEDICAL IMAGE PROCESSING APPARATUS AND METHOD THEREOF

(75) Inventors: Tomoyuki Takeguchi, Kanagawa (JP); Yukinobu Sakata, Kanagawa (JP); Shuhei Nitta, Tokyo (JP); Tomoya Okazaki, Kanagawa (JP); Takamasa Sugiura, Kanagawa (JP); Nobuyuki Matsumoto, Tokyo (JP); Yasuko Fujisawa, Tochigi (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/636,442
(22) PCT Filed: May 11, 2012
(86) PCT No.: PCT/JP2012/003093
§ 371 (c)(1), (2), (4) Date: Dec. 14, 2012
(87) PCT Pub. No.: WO2012/153539
PCT Pub. Date: Nov. 15, 2012

(65) Prior Publication Data
US 2014/0219524 A1     Aug. 7, 2014

(30) Foreign Application Priority Data

May 11, 2011   (JP) ................................. 2011-106223
Jan. 6, 2012   (JP) ................................. 2012-001524

(51) Int. Cl.
*A61B 6/00*   (2006.01)
*A61B 8/08*   (2006.01)
*G06F 19/00*  (2011.01)
*G06T 7/00*   (2006.01)
*A61B 6/03*   (2006.01)

(52) U.S. Cl.
CPC .............. *G06T 7/0085* (2013.01); *A61B 6/463* (2013.01); *A61B 6/466* (2013.01); *A61B 6/503* (2013.01);

(Continued)

(58) Field of Classification Search
CPC ...... A61B 6/503; A61B 8/0883; A61B 8/483; G06F 19/3437; G06T 2207/30048; G06T 7/0012; G06T 7/0083; G06T 7/0081
USPC .......................................................... 382/128
See application file for complete search history.

(56) References Cited

U.S. PATENT DOCUMENTS 6,106,466 A * 8/2000 Sheehan et al. ................ 600/443
7,155,042 B1 12/2006 Cowan et al.

(Continued)

FOREIGN PATENT DOCUMENTS

JP    2003 503136    1/2003
JP    2006 198410    8/2006

OTHER PUBLICATIONS

Sakata, Y., et al., "Automatic Detection of Standard Cross Section in 3D Echocardiography by using Random Trees," Proceedings of the 16th Symposium on Sensing via Image Information, IS3-24, Total 6 Pages, (Jun. 2010).

(Continued)

*Primary Examiner* — Vu Le
*Assistant Examiner* — Kenny Cese
(74) *Attorney, Agent, or Firm* — Oblon, McClelland, Maier & Neustadt, L.L.P.

(57) ABSTRACT

[Object] The invention is intended to provide a medical image processing apparatus in which improvement of accuracy of boundary detection of a heart is achieved.
[Solving Means] A medical image processing apparatus acquires volume data of a heat, detects a three-dimensional left ventricle coordinate system composed of three axes including at least a left ventricle long axis of the heart from the volume data; uses a boundary model expressed in the left ventricle coordinate system and detects a left ventricle boundary from the volume data, and displays a cross-sectional image orthogonal to at least one axis of the three axes of the left ventricle coordinate system together with the detected left ventricle boundary on the cross-sectional image.

29 Claims, 27 Drawing Sheets

(52) U.S. Cl.
CPC .............. *A61B 6/5211* (2013.01); *A61B 6/5217* (2013.01); *A61B 8/5207* (2013.01); *G06T 7/0083* (2013.01); *G06T 7/0089* (2013.01); *A61B 6/032* (2013.01); *A61B 8/0883* (2013.01); *A61B 8/483* (2013.01); *G06T 2207/10072* (2013.01); *G06T 2207/30048* (2013.01); *G06T 2207/30101* (2013.01)

(56) References Cited

U.S. PATENT DOCUMENTS

2006/0182341 A1 8/2006 Rinck et al.
2007/0014452 A1* 1/2007 Suresh et al. .................. 382/128
2010/0195881 A1 8/2010 Orderud et al.

OTHER PUBLICATIONS

Cootes, T.F., et al., "Statistical Models of Appearance for Computer Vision," Chapter 7, pp. 37-43, (Mar. 8, 2004).
Sugiura, T., et al., "An automatic contour extraction of a myocardium of the left ventricle from cardiac CT images," IEICE, pp. 1-6, (2011) (with English abstract).
International Search Report Issued Jul. 10, 2012 in PCT/JP12/03093 Filed May 11, 2012.

* cited by examiner

FIG. 4
CROSS-SECTIONAL IMAGE VERTICAL TO AXES OF VOLUME DATA
COORDINATE SYSTEM
(a) Axial View (x-y PLANE)
(b) Coronal View (z-x PLANE)
(c) Sagittal View (y-z PLANE)

FIG. 6
CROSS-SECTIONAL IMAGE VERTICAL TO AXES OF LEFT VENTRICLE
COORDINATE SYSTEM
(a) Short axis View (v-w PLANE)
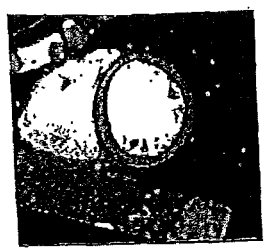
(b) 4 chamber View (u-v PLANE)
(c) 2 chamber View (w-u PLANE)

LEFT VENTRICLE BOUNDARY MODEL
EXPRESS LATITUDE, LONGITUDE DIRECTIONS AT 18 POINTS

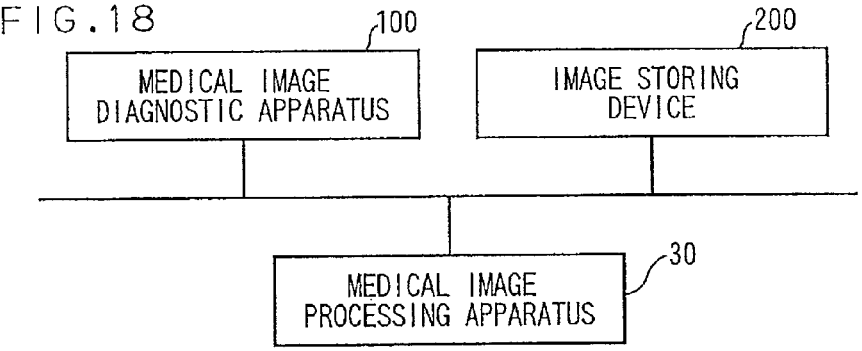
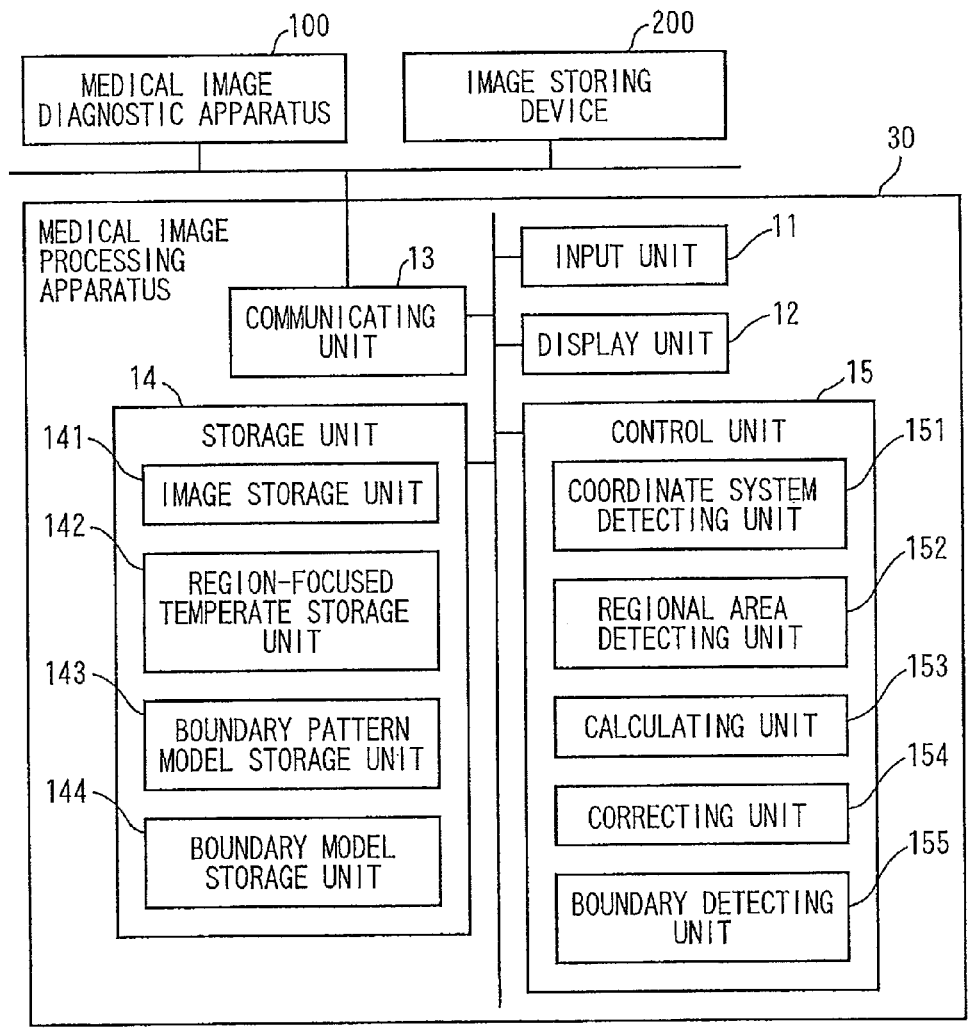

LEFT VENTRICLE
COORDINATE SYSTEM
CENTER POSITION VECTOR

SHORT AXIS VECTOR
LONG AXIS VECTOR

BOUNDARY
MODEL

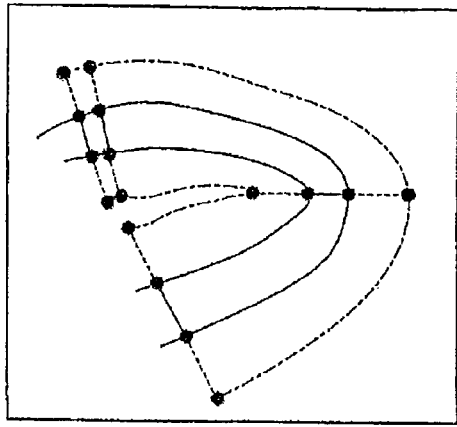
FIG. 23A
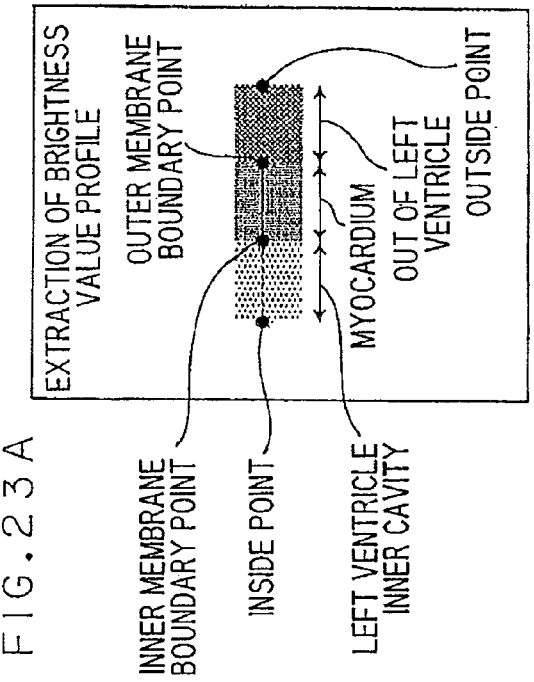
FIG. 23B
FIG. 23C

FIG.33
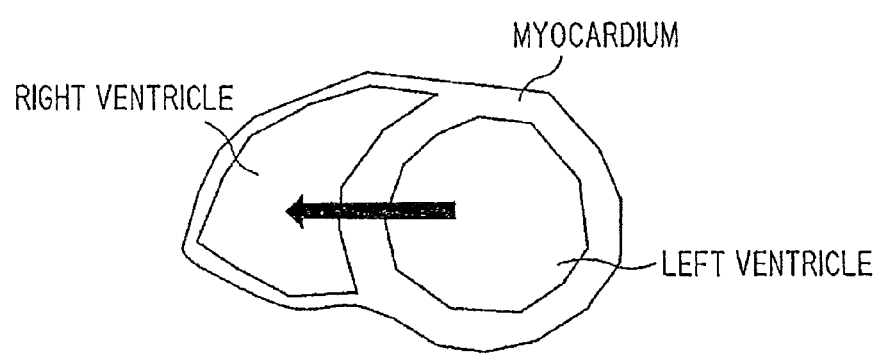
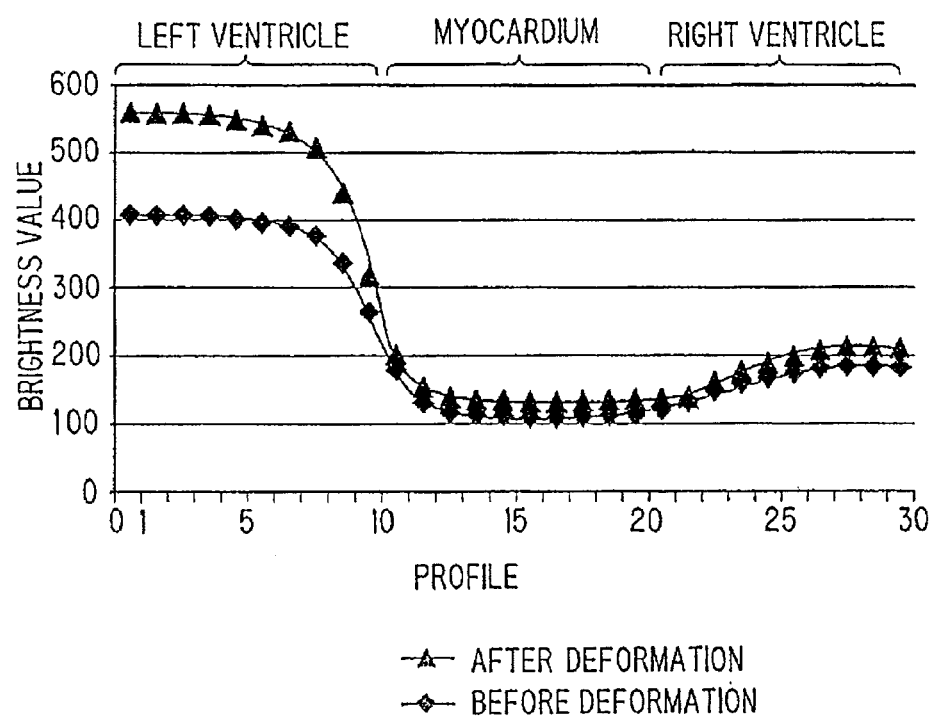

MEDICAL IMAGE PROCESSING APPARATUS AND METHOD THEREOF

TECHNICAL FIELD

The present invention relates to a medical image processing apparatus and a method thereof.

BACKGROUND ART

A medical image processing apparatus of the related art is configured to access a volume data of a heart, detect a boundary by fitting a deformable boundary model into a structure in the volume data, specify one or more characteristic points on the basis of the boundary model, and display an image of the heart on the basis of the characteristic points on a display.

CITATION LIST

Patent Literature

PTL1: JP-A-2010-179098
PTL2: U.S. Pat. No. 6,106,466

SUMMARY OF INVENTION

Technical Problem

However, in the medical image processing apparatus of the related art, since the boundary is directly detected from a volume data without performing detection or alignment of the position and the posture of the heart, there is a problem of lowering in detection accuracy.

Accordingly, an embodiment of the present invention is made in order to solve the problem described above, and it is an object of the present invention to provide a medical image processing apparatus which achieves improvement in accuracy of detection of boundaries of hearts and a method thereof.

Solution to Problem

An embodiment of the present invention is a medical image processing apparatus including: an acquiring unit configured to acquire volume data of a heart; a coordinate system detecting unit configured to detect a three-dimensional left ventricle coordinate system composed of three axes including at least a left ventricle long axis of the heart from the volume data; a boundary detecting unit configured to use a boundary model expressed in the left ventricle coordinate system to detect a left ventricle boundary from the volume data by deforming the boundary model so that an error between a boundary pattern obtained by applying the boundary model to the volume data and a predetermined boundary pattern model becomes small; and a display unit configured to display the detected left ventricle boundary on a cross-sectional image together with the cross-sectional image orthogonal to at least one axis of the three axes of the left ventricle coordinate system.

BRIEF DESCRIPTION OF THE DRAWINGS

FIG. 4 shows drawings showing cross-sectional images vertical to axes of the volume data coordinate system.

FIG. 6 shows drawings showing cross-sectional images vertical to the axes of the left ventricle coordinate system.

FIG. 18 is a drawing showing a configuration example of an image processing system in which a medical image processing apparatus according to a sixth embodiment is installed.

FIG. 19 shows an example of a configuration of a medical image processing apparatus according to a sixth embodiment.

FIG. 23 is a drawing showing an example of creation of a boundary pattern model.

FIG. 33 is a drawing showing an example of correction of a boundary pattern model.

DESCRIPTION OF EMBODIMENT

A medical image processing apparatus according to an embodiment of the present invention will be described below.

First Embodiment

Referring now to FIG. 1 to FIG. 6, a medical image processing apparatus 10 according to a first embodiment will be described. The medical image processing apparatus according to the embodiment is an apparatus configured to display images relating to hearts.

Figure 1:
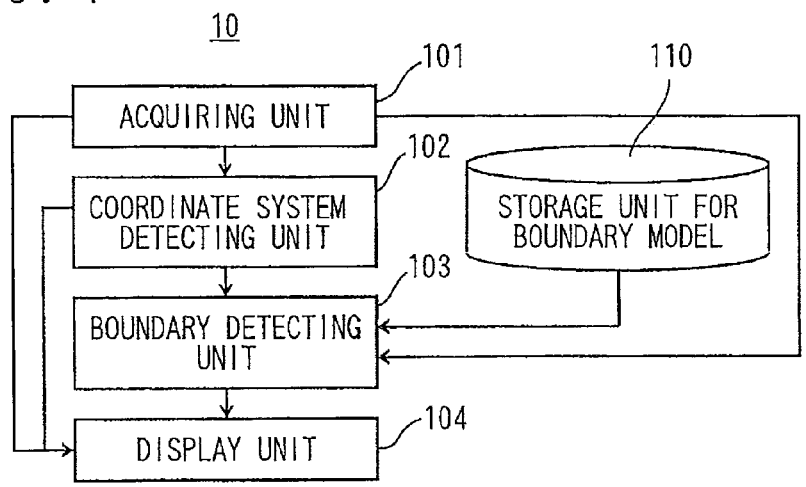
FIG. 1 is a block diagram showing a configuration of a medical image processing apparatus according to a first embodiment.

Referring now to FIG. 1, a configuration of the medical image processing apparatus 10 according to the embodiment will be described. FIG. 1 is a block diagram showing the medical image processing apparatus 10.

The medical image processing apparatus 10 includes an acquiring unit 101, a coordinate system detecting unit 102, a boundary detecting unit 103, a display unit 104, and a storage unit 110 in which a three-dimensional left ventricle boundary model (hereinafter, referred to as "boundary model") is stored.

The acquiring unit 101 acquires three-dimensional volume data relating the heart and sends the data to the coordinate system detecting unit 102, the boundary detecting unit 103, and the display unit 104.

The coordinate system detecting unit 102 is configured to detect a left ventricle coordinate system from the volume data and send the data to the boundary detecting unit 103 and the display unit 104.

The boundary detecting unit 103 is configured to detect a three-dimensional left ventricle boundary by using the boundary model recorded in the storage unit 110, and send data to the display unit 104.

The display unit 104 displays the volume data, the left ventricle coordinate system and the left ventricle boundary.

Figure 2:
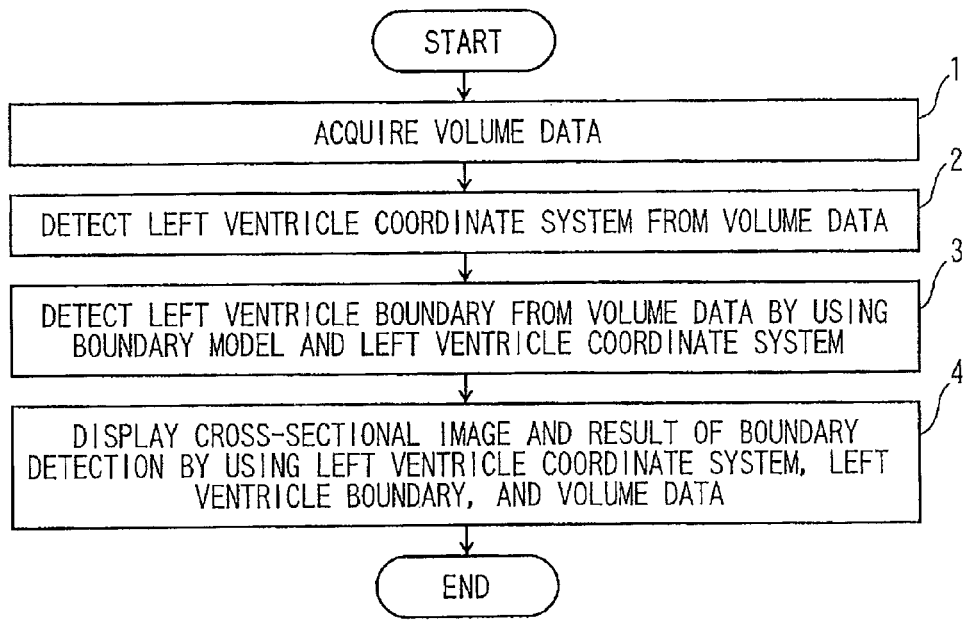
FIG. 2 is a flowchart showing an operation of the same medical image processing apparatus.

Referring to FIG. 1 and FIG. 2, an operation of the medical image processing apparatus 10 will be described. FIG. 2 is a flowchart showing the operation of the medical image processing apparatus 10.

First of all, in Step 1, the acquiring unit 101 acquires volume data in which a heart is imaged from an exterior imaging device or the like.

The term "volume data" means a grayscale image having three-dimensional extensity in a spatial direction. The three-dimensional volume data of the heart can generally be imaged by medical image processing apparatuses such as an X-ray CT apparatus, an MRI image apparatus, an ultrasonic wave diagnostic apparatus and a nuclear medicine diagnostic apparatus. However, the invention is not limited to the volume data imaged by these imaging apparatuses. The volume data can be acquired directly from the imaging apparatus and may be acquired from external media such as servers, personal computers, HDDs, and DVDs in which picked-up image data are stored.

The volume data acquired by the acquiring unit 101 is sent to the coordinate system detecting unit 102, the boundary detecting unit 103, and the display unit 104. At this time, a denoising process, a contrast emphasizing process, and an image enlargement or reducing process may be performed on the volume data so as to be suitable for the respective process steps. However, when performing image enlargement or reducing process, a scale reduction relationship among volume data to be sent to the respective units is stored.

Subsequently, in Step 2, the coordinate system detecting unit 102 detects a left ventricle coordinate system from the volume data sent from the acquiring unit 101.

Figure 3:
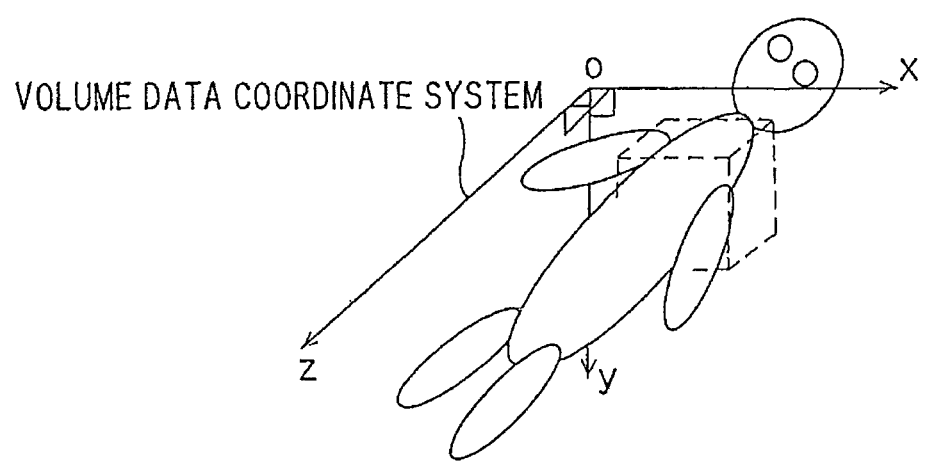
FIG. 3 is a drawing showing a volume data coordinate system with reference to a human body.
Figure 5:
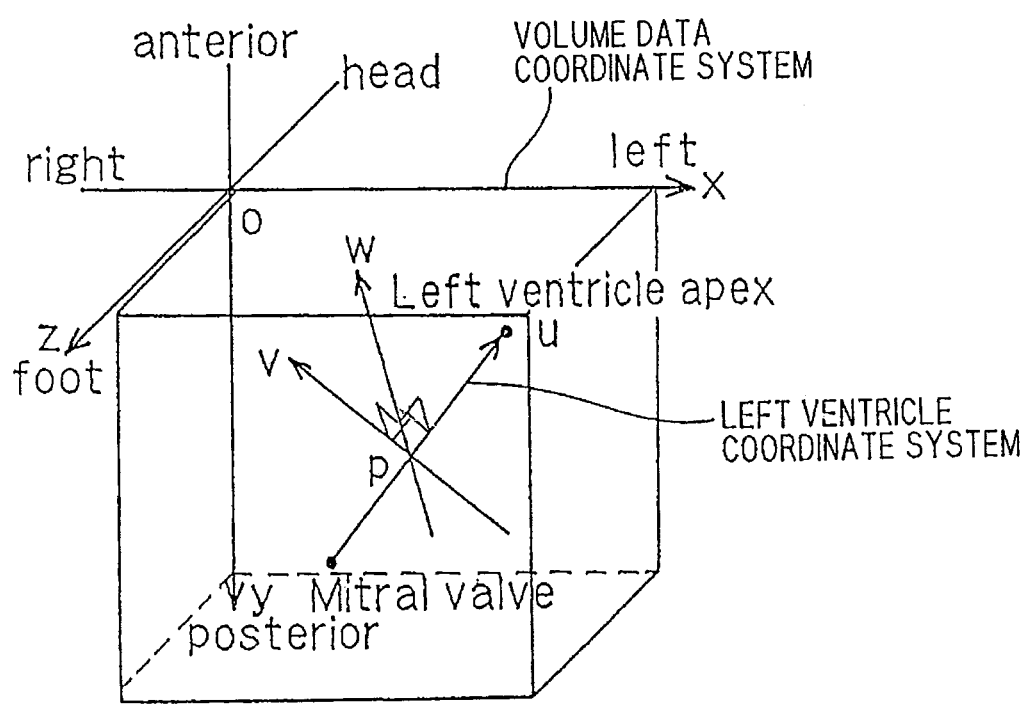
FIG. 5 is a drawing showing a left ventricle coordinate system overlapping with the volume data coordinate system.

The term "left ventricle coordinate system" corresponds to a three-dimensional coordinate system including three axes including at least a left ventricle long axis (hereinafter, refereed to simply as "long axis"). FIG. 3 to FIG. 6 show a relationship between the left ventricle coordinate system and a volume data coordinate system. FIG. 3 is a drawing showing the volume data coordinate system with reference to a human body, FIG. 4 shows drawings showing a cross-sectional image vertical to axes of the volume data coordinate system, FIG. 5 is a drawing showing the volume data coordinate system and the left ventricle coordinate system overlapping with each other, and FIG. 6 is a drawing showing a cross-sectional image vertical to the axis of the left ventricle coordinate system.

The volume data is generally stored on the basis of the volume data coordinate system with reference to a coordinate system of the imaging device. As shown in FIG. 3, the volume data coordinate system includes a direction of body axis (z-axis), a dorsal-ventral direction (y-axis) and a left-and-right direction (x-axis) of a human body when the volume data is imaged by, for example, the CT apparatus. As shown in FIG. 4, cross-sectional images orthogonal to the direction of these axes are referred to as Axial View, Sagittal View, and Coronal View.

In the volume data of the imaged heart, the existing position, the direction, and the size of the heart in the volume data varies depending on individual differences, breathing, cardiac beats, the relative positional relationship between the apparatus and the human body at the time of imaging. Therefore, the position and the posture of the heart need to be specified in the volume data.

Figure 7:
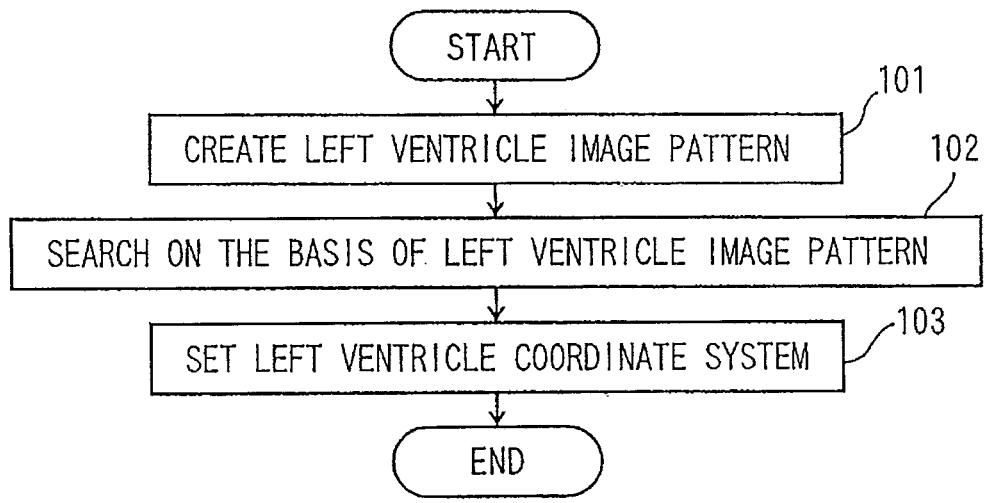
FIG. 7 is a flowchart of a first detecting method of the coordinate system detecting unit.

Detection of the left ventricle coordinate system is performed for setting the position and direction of the left ventricle in the volume data. As a first detecting method of the left ventricle coordinate system, for example, there is a method indicated in Non Patent Literature 1 ("Automatic Detection of Reference Cross Section for Diagnosis from Cardiac Echo Volume Data by using Random Tree" by Yukitatsu Sakata (IS3-24, Image Sensing Symposium proceedings, The 16th image sensing Symposium). Referring now to FIG. 5 to FIG. 8, the first detecting method will be described. FIG. 7 is a flowchart of the first detecting method.

In Step 101, the coordinate system detecting unit 102 sets the left ventricle coordinate system to the long axis (u-axis), an axis (v-axis) orthogonal to the left ventricle which sets a cross section which allows observation of a 4 chamber View, and an axis (w-axis) orthogonal to the two axes in advance as shown in FIG. 5, and prepare a left ventricle cross-sectional image pattern with reference to the left ventricle coordinate system configured with a center P of the left ventricle in advance as shown in FIG. 5. The term "the left ventricle cross-sectional image pattern" means a left ventricle cross-sectional image used in pattern matching.

Figure 8:
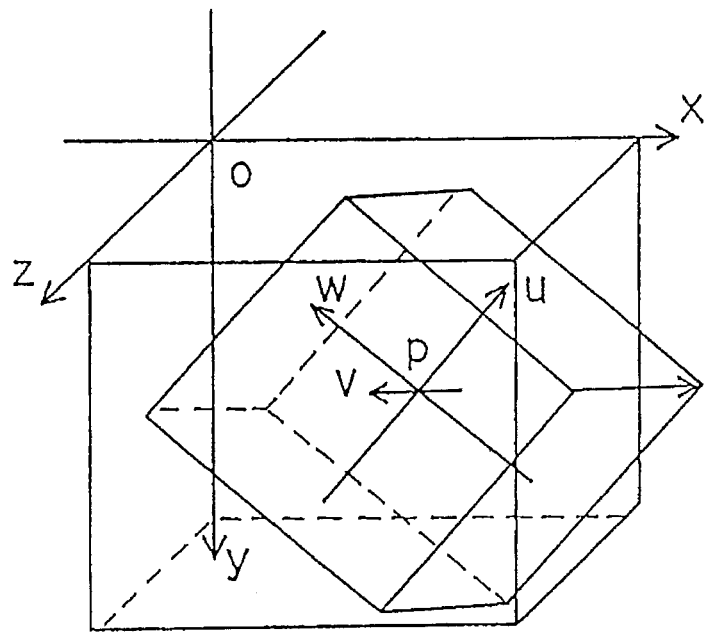
FIG. 8 is an explanatory drawing of a left ventricle coordinate system to be detected.

Subsequently, in Step 102, the coordinate system detecting unit 102 searches a position, a posture and a scale which are matched best while applying the left ventricle cross-sectional image pattern to the volume data, thereby setting the left ventricle coordinate system from the volume data as shown in FIG. 8.

Figure 9:
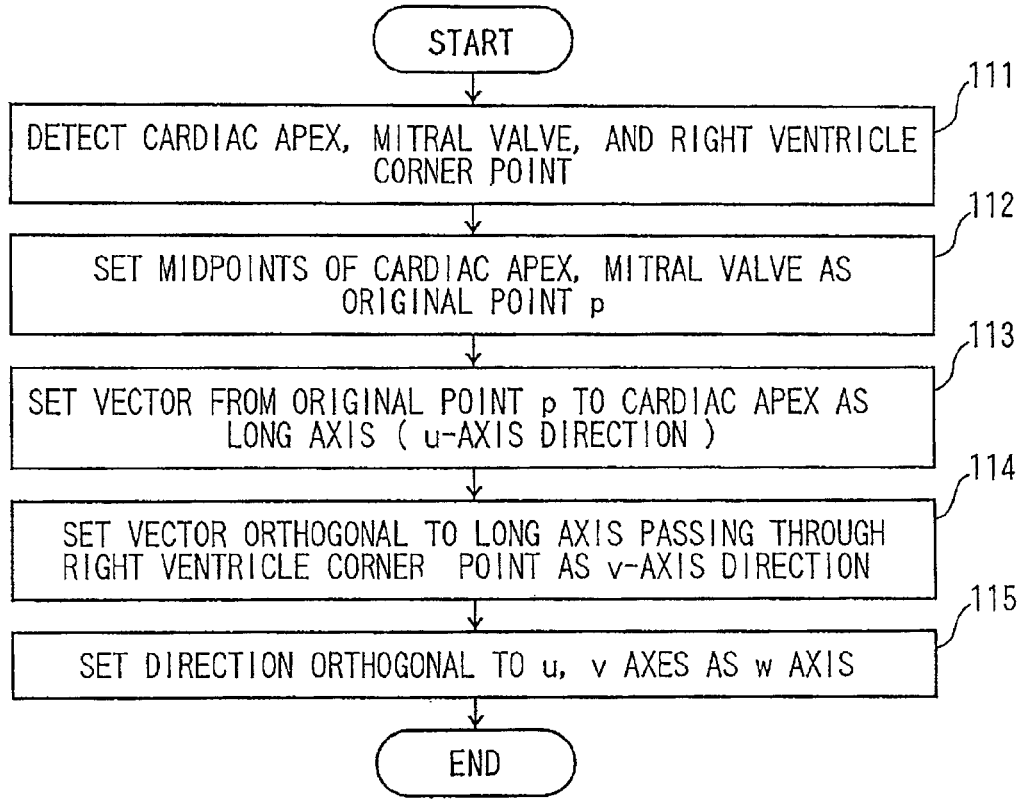
FIG. 9 is a flowchart of a first detecting method of the coordinate system detecting unit.
Figure 10:
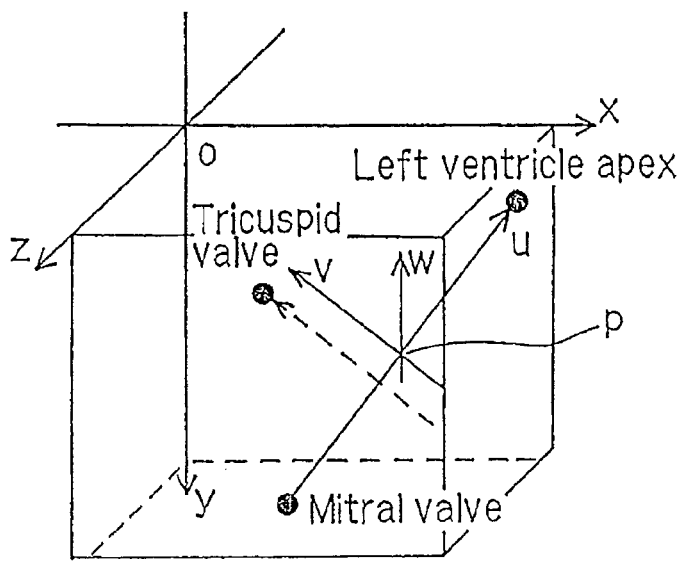
FIG. 10 is an explanatory drawing of a left ventricle coordinate system to be detected.

Referring now to a flowchart in FIG. 9 and FIG. 10, a second detecting method of the left ventricle coordinate system will be described. The three-dimensional coordinate system can be set with three points which are not aligned on one straight line in a three-dimensional space.

In Step 111, the coordinate system detecting unit 102 detects the position of the cardiac apex, the position of a mitral valve, and a right ventricle corner point from the volume data. In this detecting method, the coordinate system detecting unit 102 detects the position of the cardiac apex by performing the pattern matching between the volume data and an image pattern in the surround of the position of the cardiac apex learned in advance. For reference, the term "image pattern" means an image used in the pattern matching. In the same manner, the coordinate system detecting unit 102 detects the position of the mitral valve and the right ventricle corner point also by the pattern matching between the volume data and the image pattern in the surround of the position of the mitral valve and the image pattern in the surround of the right ventricle corner point.

Subsequently, in Step 112, the coordinate system detecting unit 102 sets an intermediate point between the position of the cardiac apex and the position of the mitral valve from the volume data as an original point p.

Subsequently, in Step 113, the coordinate system detecting unit 102 sets a vector from the original point p to the position of the cardiac apex as the long axis (u-axis) (See FIG. 10).

Subsequently, in Step 114, the coordinate system detecting unit 102 sets a vector orthogonal to the long axis (u-axis) and passing through the right ventricle corner point as the second axis (v-axis) (see FIG. 10). The right ventricle corner point can be detected by performing the matching with respect to the image pattern learned in advance in a cross section orthogonal to the detected long axis.

Subsequently, in Step 115, the coordinate system detecting unit 102 sets a direction orthogonal respectively to the long axis (u-axis) and the second axis (v-axis) as the third axis (w-axis) (see FIG. 10).

For reference, the left ventricle coordinate system can be set not only by detecting the right ventricle corner point, but by detecting the position of a tricuspid valve, or the position of a left ventricle outflow tract in the same manner as another point in the heart.

The method of detecting the left ventricle coordinate system is not limited thereto, and any detecting method is applicable as long as the three-dimensional coordinate system having the long axis as one of the components can be set.

Also, as is clear from the embodiment, it is not necessary to use a point on a left ventricle boundary to be detected in a downstream step or a point to be set by the left ventricle boundary for detecting the left ventricle coordinate system.

Subsequently, in Step 3, the boundary detecting unit 103 detects the left ventricle boundary from the volume data acquired by the acquiring unit 101 by using the left ventricle coordinate system acquired by the coordinate system detecting unit 102 and a boundary model stored in the storage unit 110.

The "left ventricle boundary to be detected by the boundary detecting unit 103" means one of an inner membrane boundary which is a boundary between a myocardium surrounding the left ventricle (a gray region surrounded by a solid line in FIG. 6) and a left ventricle cavity (white region) and an outer membrane boundary which is a boundary between the myocardium surrounding the left ventricle and the out of the left membrane, or both of the boundaries. FIG. 6(a) is a Short Axis View (plan view along v-w), (b) is a 4 chamber View (plan view along u-v) and (c) is a 2 chamber View (plan view along w-u). In the embodiment, a case where only an inner boundary (an inner myocardial boundary) is detected as the left ventricle boundary will be described.

Figure 11:
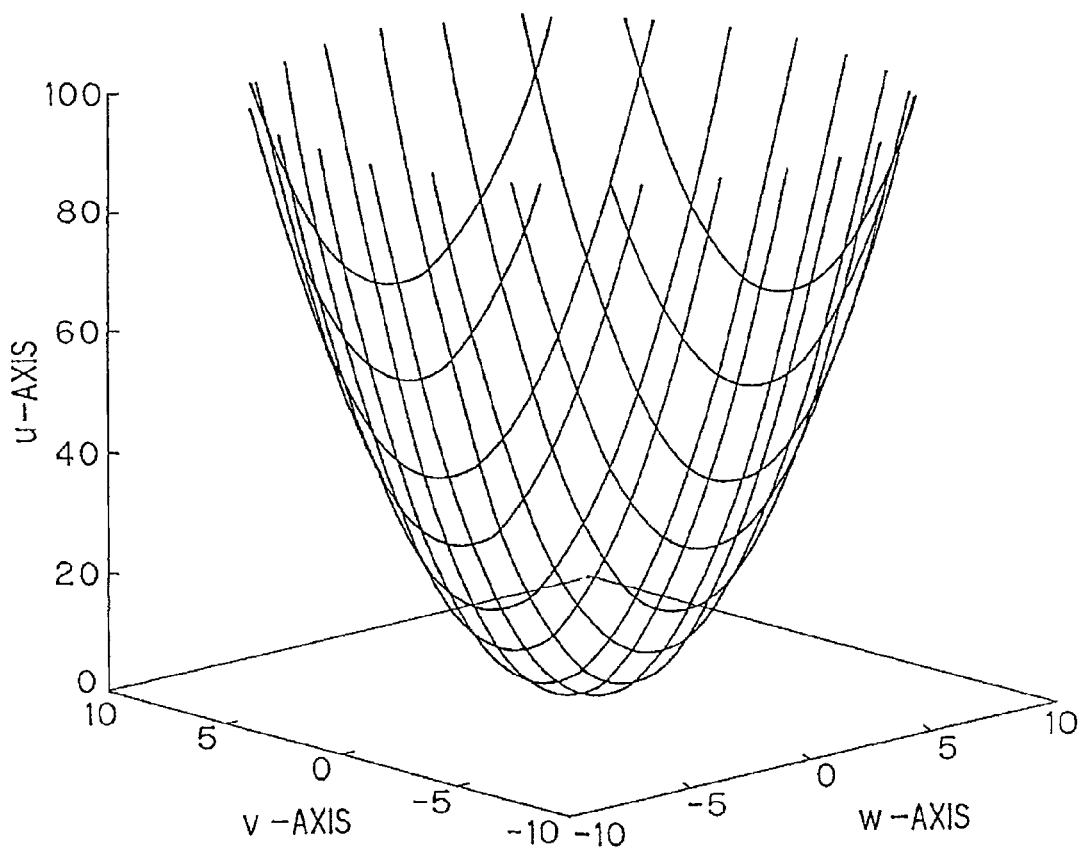
FIG. 11 is a drawing showing an example of a boundary model.

The inner membrane boundary of the left ventricle can be approximated by a cup-shaped boundary model having an apex at the position of the cardiac apex. The boundary model may be approximated with a secondary curved surface having a center axis along the long axis (u-axis), for example, as shown in FIG. 11 on the assumption that the left ventricle coordinate system is already detected. The boundary model in FIG. 11 is expressed as an expression (1).

[Expression 1]

$$u = a1*v^2 + a2*w^3 + a3 \qquad (1)$$

where u<a4. This boundary model includes four variables of a1, a2, a3, and a4, and a projecting shaped rotational paraboloidal surface can be defined on the left ventricle coordinate system. Therefore, detection of the boundary of the embodiment means to acquire variations (parameter) a1, a2, a3, and a4 of the boundary model in the volume data in which the three-dimensional left ventricle coordinate system is obtained. The boundary models in FIG. 11 are a1=1, a2=1, a3=0, and a4=100.

A method of obtaining the variables a1 to a4 is to define energy which can be calculated between a boundary model and the volume data, giving initial values to the variables, and optimizing the variables repeatedly so that the defined energy becomes smaller. Application of the boundary model on the basis of minimization of the energy as described above is a general method, and is used as a method of application of snakes or an active contour model.

However, the embodiment is characterized in that the boundary model is premised on detection of the left ventricle coordinate system. In other words, detection of the left ventricle coordinate system enables not only an expression of the three-dimensional shape in a simple form as in the expression (1), but also a device such as limiting the range of variables by obtaining a prior distribution of the respective variables in advance. Also, when the left ventricle coordinate system is detected, rough regions of myocardium of the left ventricle such as a side wall, a front wall, a lower wall, and a septula can be specified, so that a device for improvement of accuracy on the basis of the process according to the region, such as defining different energy with respect to the specific region, is also enabled.

The boundary detecting unit 103 renews the variables from a1 to a4 until the differential amount of brightness in the normal direction at a point on the three-dimensional boundary is increased. Since the normal direction has three dimensions as a matter of course, calculation of energy is enabled by calculating the differential amount (amount of difference) in the three-dimensional directions in the volume data. General search algorithm such as Greedy Algorithm, Simulated Annealing, and Heredity Algorithm can be used as a method of renewing the model parameter required for minimization of energy.

Finally, in Step 4, the display unit 104 displays the volume data obtained by the acquiring unit 101, the left ventricle coordinate system obtained by the coordinate system detecting unit 102, and the three-dimensional left ventricle boundary obtained by the boundary detecting unit 103 on a display device such as a display, a projector, or a printer. The display unit 104 needs only to be capable of displaying the cross-sectional image of the volume data and the detected boundary and is not limited to the device described above.

The cross section of the volume data displayed on the display unit 104 is determined on the basis of the left ventricle coordinate system. The cross-section orthogonal to the long axis (u-axis) of the left ventricle coordinate system is a general left ventricle short-axis image for a user (medical staff). Here, by displaying the left ventricle boundary at the same cross-sectional position, the result of boundary detection can be confirmed on a cross-sectional image which allows the user to recognize the position and the posture of the heart easily.

Also, by detecting the long axis (u-axis) direction and the direction by which the 4 chamber View can be defined (v-axis direction) as the left ventricle coordinate system, the 4 chamber View and the left ventricle boundary on the cross section can be displayed in addition to the short-axis image, so that a general image of the result of detection of the three-dimensional boundary or the result of detection of the left ventricle coordinate system can be figured out further easily. In the same manner, the same effects are obtained also by detecting the V-axis as the direction for defining a 3 chamber View and the 2 chamber View.

Also, by setting the left ventricle coordinate system to be detected to an orthogonal coordinate system and setting the original point p of this coordinate system to the estimated center of the left ventricle, three cross sections indicated by u=0, v=0, and w=0 are two cross sections including the long axis and a short-axis cross section about the center of the left ventricle as the center of the cross-sectional image. Since the cross-sectional images are orthogonal to each other, the positional relationship can be figured out easily, and whether the left ventricle coordinate system as well as the detected left ventricle boundary are correct or not can be confirmed easily.

According to the embodiment, detection of the boundary with high degree of accuracy is enabled by detecting the left ventricle coordinate system by the coordinate system detecting unit 102 and detecting the left ventricle boundary by the boundary detecting unit 103 on the basis of the left ventricle coordinate system, so that the confirmation of the result of the boundary detection can be displayed easily by the display unit 104.

Second Embodiment

The medical image processing apparatus 10 according to a second embodiment will be described by using a block diagram in FIG. 12. The medical image processing apparatus 10 according to the embodiment is a first modification of the medical image processing apparatus 10 according to the first embodiment.

In the medical image processing apparatus 10 of the embodiment, the coordinate system detecting unit 102 converts the coordinate of the volume data obtained by the acquiring unit 101 into the detected left ventricle coordinate system, thereby simplifying subsequent operations.

Figure 12:
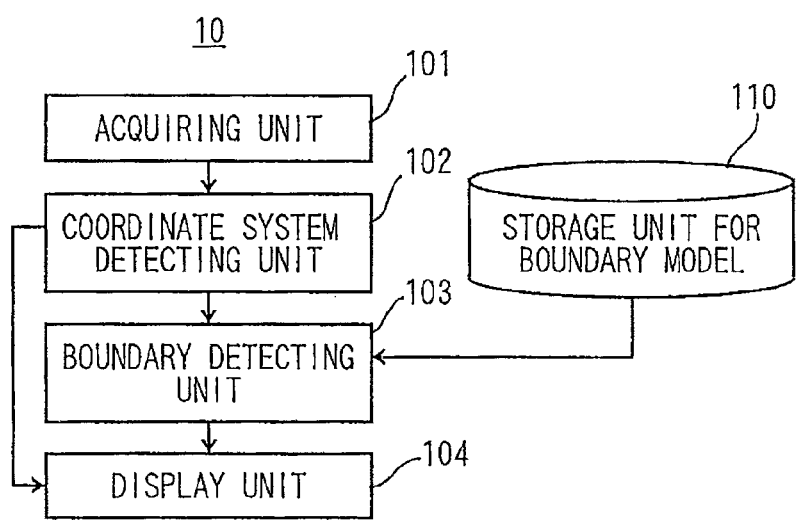
FIG. 12 is a block diagram showing a configuration of a second embodiment.

Since the coordinate system detecting unit 102 provides an image after the coordinate conversion to the boundary detecting unit 103 and the display unit 104, it is no longer necessary to provide the volume data from the acquiring unit 101, so that a data flow can be simplified as shown in FIG. 12.

Third Embodiment

The medical image processing apparatus 10 according to a third embodiment will be described. The medical image processing apparatus 10 according to the embodiment is a second modification of the medical image processing apparatus 10 according to the first embodiment.

Although the method of detecting the inner membrane boundary of the left ventricle (the inner myocardial boundary) by the boundary detecting unit 103 has been described in the first embodiment, it is also applied to detection of the outer membrane (an outer myocardial boundary) in the same manner.

In other words, in the embodiment, the storage unit 110 stores a boundary model relating to the inner membrane boundary and a boundary model relating to the outer membrane boundary respectively, whereby the boundary detecting unit 103 is capable of performing the detection of the boundaries of the inner membrane and the outer membrane independently, so that the period required for the boundary detection is reduced by using a parallel computer.

The boundary detecting unit 103 may perform the detection of the inner membrane boundary and the outer membrane boundary integrally by configuring the storage unit 110 to store the boundary model composed of integrally combined inner membrane boundary and outer membrane boundary.

Fourth Embodiment

Referring now to FIG. 13 to FIG. 17, a medical image processing apparatus 20 according to a fourth embodiment will be described.

Figure 13:
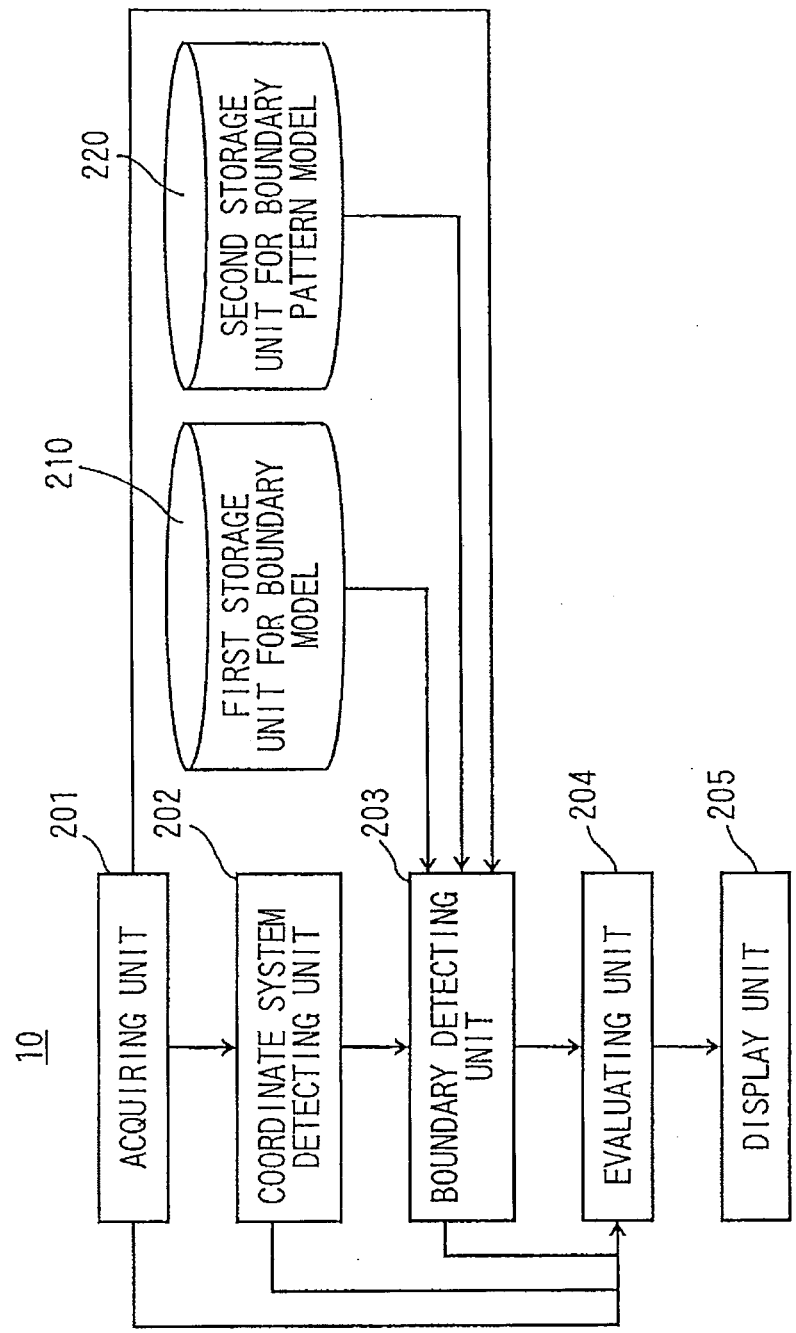
FIG. 13 is a block diagram showing a configuration of a medical image processing apparatus according to a fourth embodiment.

Referring now to FIG. 13, a configuration of the medical image processing apparatus 20 according to the embodiment will be described. FIG. 13 is a block diagram showing the medical image processing apparatus 20.

The medical image processing apparatus 20 includes an acquiring unit 201 configured to acquire the volume data, a coordinate system detecting unit 202 configured to detect the left ventricle coordinate system, a boundary detecting unit 203 configured to detect the boundary of the left ventricle, a evaluating unit 204 configured to evaluate the detected left ventricle boundary, a display unit 205 configured to display the result of evaluation, a first storage unit 210 configured to store the boundary model, and a second storage unit 220 configured to store the boundary pattern model.

Figure 15:
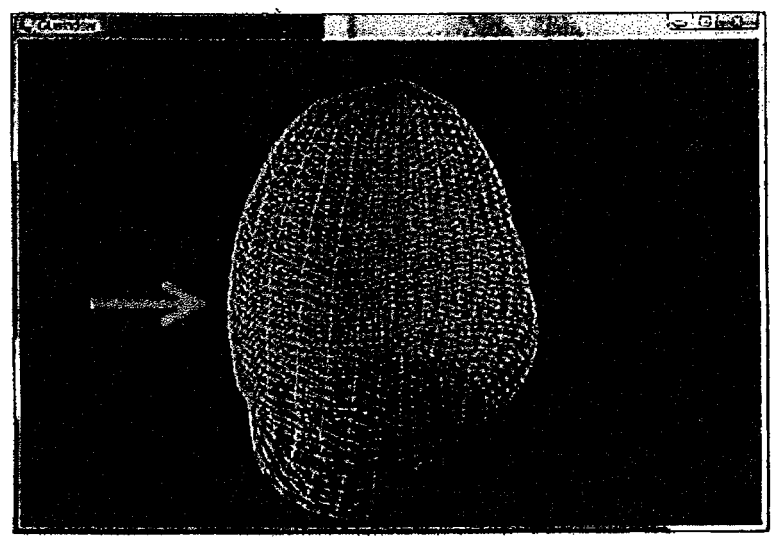
FIG. 15 is an explanatory drawing showing a boundary model.

First of all, the "boundary model" in the embodiment will be described. The boundary model is expressed by a plurality of base vectors obtained by analyzing principle component of a three-dimensional boundaries instructed to a plurality of volume data collected in advance and a linear sum of an average shape. This method of expression is disclosed in Non Patent Literature 2 (T. F. Cootes and C. J. Taylor, "Statistical Models of Appearance for Computer Vision", http://personalpages.manchester.ac.uk/staff/timothy.f.cootes/Models/app_models.pdf) referred to as Active Shape Model. This method of expression is capable of handling the inner and outer boundaries simultaneously by handling the coordinate of a point on the inner and outer boundaries as one vector. However, in the embodiment, alignment by using the left ventricle coordinate system may be performed by premising that the left ventricle coordinate system is already detected. When learning the boundary model, the left ventricle coordinate systems and the three-dimensional boundaries are instructed for the plurality of volume data collected in advance. Since the boundaries instructed to the plurality of volume data are expressed by independent three-dimensional image coordinate systems, even when the two boundaries have completely the same shape, the shape vectors of the boundaries have different values when the positions on the respective images are different. Therefore, normalization of the shapes of the boundaries by using the left ventricle coordinate systems is performed and the difference between the coordinate system of the boundary shape vectors is absorbed. The normalization is achieved by converting a point on the boundary into left ventricle coordinate systems in the respective volume data. When by using the boundary model on the volume data, the coordinate of the boundary model is converted into the left ventricle coordinate system detected from the volume data. FIG. 15 is a drawing showing the boundary model learned in this manner, and is the boundary model of the left ventricle expressed with 18 points in the long axis and the short axis directions.

Figure 16:
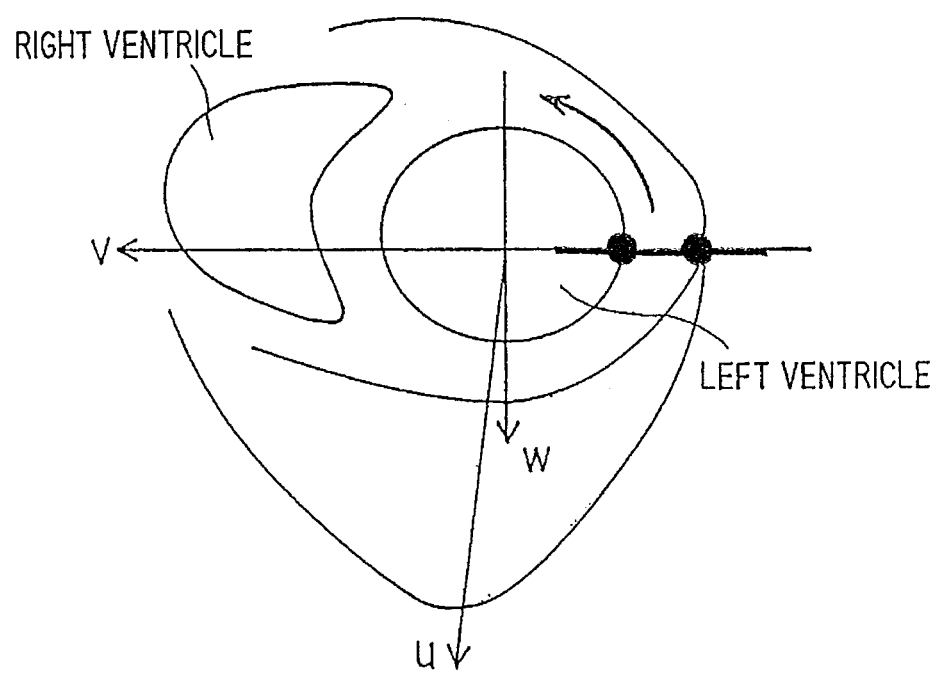
FIG. 16 is a view along a plane v-w of a heart showing a boundary pattern model.
Figure 17:
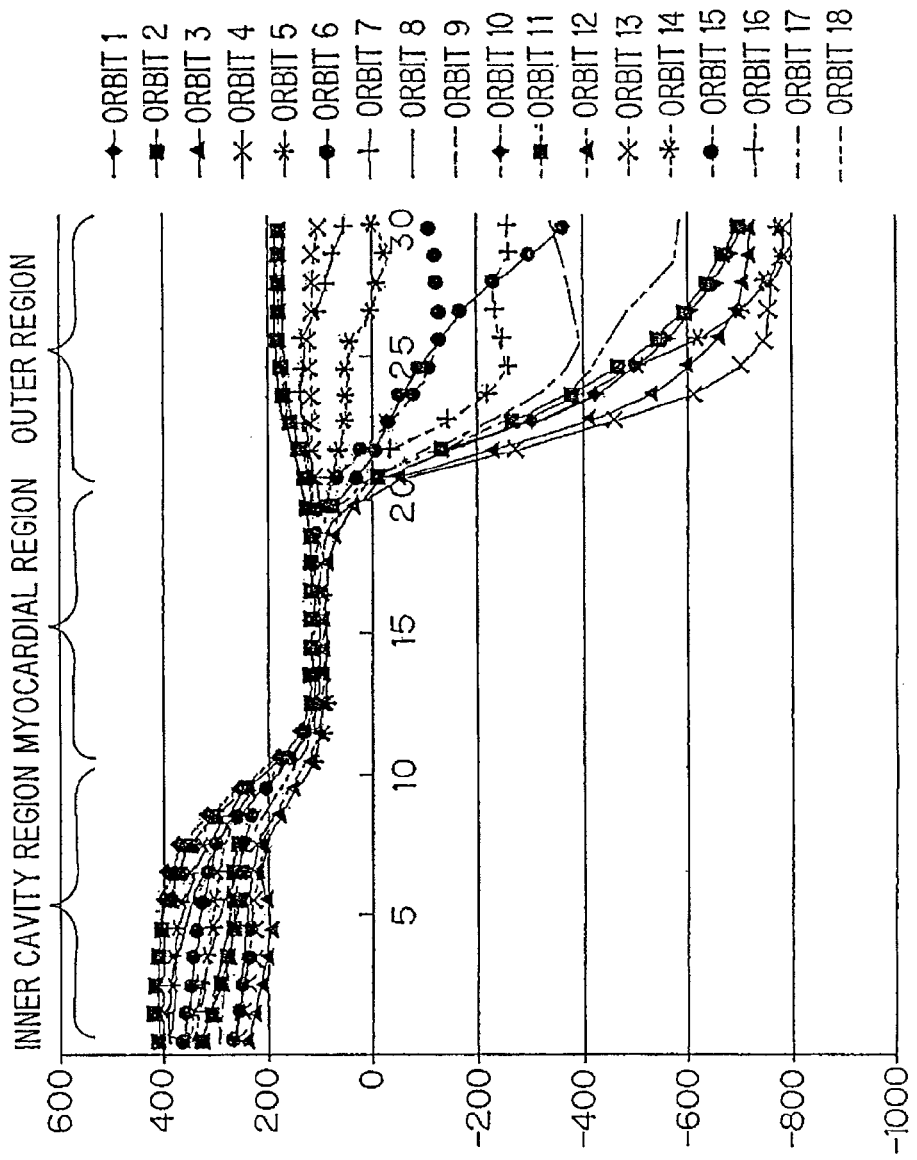
FIG. 17 is a graph showing a boundary pattern model.

Subsequently, the "boundary pattern model" will be described. The boundary pattern model is an image pattern of the surround of the three-dimensional boundary. The second storage unit 220 collects the boundary patterns of the surround of the three-dimensional boundaries instructed to a plurality of learning volume data collected in advance, and learns the same as a boundary pattern model. Referring now to FIG. 16 and FIG. 17, the learning of the boundary pattern model will be described.

FIG. 16 is a view of a heart along the plane v-w. A graph in FIG. 17 has a vertical axis indicating pixel values (for example, values of brightness) and a lateral axis indicating a straight line penetrating through the inner and outer boundaries divided by a plurality of points (30 points in the drawing), and numbers (1 to 30 in the drawing) are assigned to the respective points. In other words, in FIG. 16, a point inside the myocardium region of the heart corresponds to No. 10 in FIG. 17, and a point on the outside thereof corresponds to No. 20. Also, the cross-sectional view taken along the plane v-w in FIG. 16 is divided into 18 parts at regular angle in the circumferential direction (the direction indicated by an arrow) about an original point p, and patterns of pixel values obtained by profiling 30 points on straight lines at respective divided positions correspond to orbits 1 to 18 in FIG. 17. Then, the patterns of the pixel values indicated by the respective orbits in FIG. 17 correspond to patterns obtained by averaging patterns of the pixel values of the respective orbits collected from the plurality of learning volume data (hereinafter, referred to as "boundary patterns"). Then, the averaged patterns (boundary patterns) exist by a number of points on the boundary in the long axis (u-axis) direction (18 points), these boundary patterns are collectively referred to as a boundary pattern model.

In other words, profiles each relating to a linear image passing through two points having the same point number (the same orbit number) as shown in FIG. 16 are stored from the plurality of learning volume data. As there exist the same number of the profiles relating to the linear image passing through the two points on the same point number (the same orbit number) as the number of the plurality of learning volume data. Therefore, the boundary patterns as shown in FIG. 17 which are obtained by averaging the respective pixel values of these profiles are created. As there are the same number of the boundary patterns as the points on the boundary in the u-axis direction, these boundary patterns are collectively referred to as a boundary pattern model.

Figure 14:
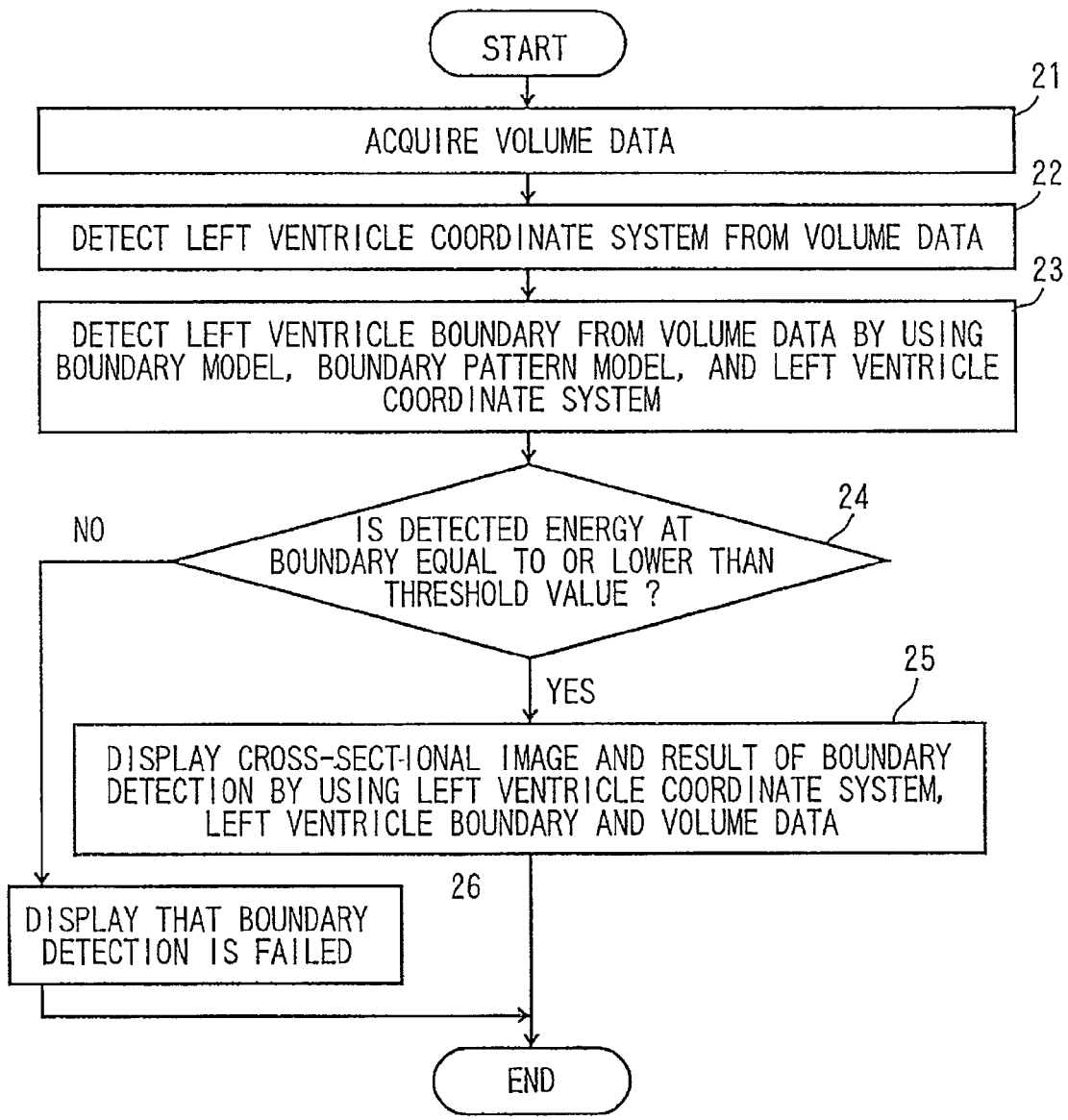
FIG. 14 is a flowchart showing an operation of the same medical image processing apparatus.

Referring to FIG. 13 and FIG. 14, an operation of the medical image processing apparatus 20 will be described. FIG. 14 is a flowchart showing the operation of the medical image processing apparatus 20.

First of all, in Step 21, the acquiring unit 201 acquires volume data in which a heart is imaged.

Subsequently, in Step 22, the coordinate system detecting unit 202 detects a left ventricle coordinate system from the volume data obtained from the acquiring unit 201. This detecting method is the same as that in the first embodiment.

Subsequently, in Step 23, the boundary detecting unit 203 detects the left ventricle boundary from the volume data acquired by the acquiring unit 201 by using the left ventricle coordinate system acquired by the coordinate system detecting unit 202, the boundary model stored in the first storage unit 210 and the boundary pattern model stored in the second storage unit 220. The boundary detecting unit 203 in the embodiment detects the inner membrane boundary and the outer membrane boundary of the left ventricle in the following manner.

First of all, the boundary detecting unit 203 applies the boundary model expressed by Active Shape Model to a volume data.

Secondly, the boundary detecting unit 203 obtains a boundary pattern at a position of the boundary model applied to the volume data (hereinafter, referred to as "input boundary pattern"). The input boundary pattern is expressed by the pixel values in the volume data.

Thirdly, the boundary detecting unit 203 obtains energy required for detecting the boundary. This energy obtains an error between the input boundary pattern and the boundary pattern model described above. Examples of the "error" include, for example, a squared error, an absolute sum, and a difference between brightness values of respective pixels of the input boundary pattern and brightness values of respective pixels in the boundary pattern model.

Fourthly, the boundary detecting unit 203 deforms the boundary model expressed by Active Shape Model so as to lower the energy. Deformation is, for example, such that the weight of the linear sum of an average shape expressing Active Shape Model is changed. Lowering the energy is equivalent to deforming the boundary model so as to be similar to the boundary pattern model.

Fifthly, the boundary detecting unit 203 obtains a boundary model deformed so that the energy (the error between the boundary pattern and the boundary pattern model) is minimized. Then, the inner membrane boundary and the outer membrane boundary detected by the boundary model are the inner membrane boundary and the outer membrane boundary to be detected finally.

Subsequently, in Step 24, the evaluating unit 204 performs a comparison of the minimized energy (hereinafter, referred to as "final energy") with a predetermined threshold value. The display unit 205 may display the result of comparison with the threshold value (that is, the result of evaluation). Here, whether or not the result is lower than the threshold value and, depending on the result, the procedure as shown below is performed. When the final energy is equal to or lower than the threshold value, the procedure goes to Step 25 (if Yes). When the minimum energy is higher than the threshold value, the procedure goes to Step 26 (if No).

In Step 25, since the minimum energy is equal to or lower than the threshold value, the display unit 205 displays a cross-sectional image and a result of boundary detection by using the left ventricle coordinate system, the left ventricle boundary and the volume data.

In Step 26, since the minimum energy is higher than the above-described value, the display unit 205 notifies the user of the fact that the probability that the detection of the boundary is not accurate is high. In other words, the high final energy means that the left ventricle boundary is detected at a position showing a pattern different from the boundary pattern model. In this case, since it is determined that the correct boundary position is not detected because the detection of the left ventricle coordinate system is wrong, a message stating that the left ventricle boundary cannot be detected is displayed. In this case, detection of the left ventricle coordinate system may be performed automatically again after having changed the criteria.

According to the embodiment, detection of the boundary with high degree of accuracy is enabled by detecting the left ventricle coordinate system by the coordinate system detecting unit 202 and detecting the left ventricle boundary by the boundary detecting unit 203 on the basis of the left ventricle coordinate system, so that the confirmation of the result of the boundary detection can be displayed easily by the display unit 205 and, in addition, a failsafe function such as displaying after determination of whether the result of the boundary detection is right or wrong, or retrying the process is provided.

Although the boundary pattern model has been described above by using the pattern obtained by averaging the plurality of learning volume data, the boundary pattern model can be constructed by using a known pattern discriminating technology such as standard variations, a covariance and a subspace between the boundary patterns or a discriminator which learns by using collected profiles relating to the boundaries and the profile which has no relation to the boundaries as long as the profile relating to the image from the plurality of learning volume data is collected.

Fifth Embodiment

The medical image processing apparatus 20 according to a fifth embodiment will be described.

The medical image processing apparatus 20 according to the embodiment is a first modification of the medical image processing apparatus 20 according to the fourth embodiment.

In the embodiment, the failsafe function is provided for an automatic detecting process. For example, when the volume data to be acquired by the acquiring unit 201 does not sufficiently figure out the entire heart or is not an actually imaged heart, there are cases where detection of the left ventricle coordinate system is failed depending on the content of the volume data itself. When the detection of the left ventricle coordinate system is failed, the display unit 205 notifies the user the fact that the left ventricle coordinate system cannot be detected. Then, the operation error can be alleviated with the provision of a mechanism which encourages the user to confirm whether the volume data used for the detection of the left ventricle coordinate system is adequate by displaying the volume data with reference to the image coordinate system.

Also, as shown in Step 26 of the fourth embodiment, a notification of the failure of the boundary detection may be provided to the user by evaluating the detected final energy at the left ventricle boundary and the threshold value in a final evaluation to be performed after the boundary detecting process. In this case, by displaying only the volume data but not the detected boundary, the user is allowed to check whether the volume data is adequate or not easily.

When the left ventricle coordinate system cannot be detected correctly although the volume data is adequate, the left ventricle coordinate system can be detected again with predetermined different criteria. The term "the different criteria" here means to change a range for searching the left ventricle coordinate system, a random number to be used for search, or the boundary model to be used.

When the medical image processing apparatus 20 cannot detect the correct left ventricle coordinate system, it is also possible to make the user to set the left ventricle coordinate system. In this case, it is achieved by providing a user interface which allows the user to instruct the left ventricle coordinate system and, after having instructed, executing the boundary detecting process again.

As described above, the failsafe function can be provided for failures in associating with full automatic detection.

Sixth Embodiment

Referring now to FIG. 18 to FIG. 35, a medical image processing apparatus 30 according to a sixth embodiment will be described.

First of all, a configuration example of an image processing system in which the medical image processing apparatus 30 according to the sixth embodiment is installed will be described. FIG. 18 is a drawing showing a configuration example of an image processing system in which the medical image processing apparatus 30 according to the sixth embodiment is installed.

The image processing system shown in FIG. 18 includes a medical image processing apparatus 100, an image storing device 200, and the medical image processing apparatus 30. The respective apparatuses illustrated in FIG. 18 are in a state of being capable of communicating with each other directly or indirectly by a hospital LAN (Local Area Network) installed in a hospital. For example, when PACS (Picture Archiving and Communication System) is introduced in the image processing system, the respective apparatuses perform mutual transmission of medical image or the like in conformity to DICOM (Digital Imaging and Communications in Medicine) standard.

The medical image diagnostic apparatus 100 is an X-ray diagnostic apparatus, an X-ray CT (Computed Tomography) apparatus, an MRI (Magnetic Resonance Imaging) apparatus, an ultrasonic wave diagnosis apparatus, or an apparatus group thereof. Medical images scanned by the medical image diagnostic apparatus 100 include two-dimensional image data or three-dimensional image data (volume data). Alternatively, the medical images scanned by the medical image diagnostic apparatus 100 include two-dimensional video data or three-dimensional video data of these image data scanned along the time series. Photography performed by the X-ray CT apparatus which is an example of the medical image diagnostic apparatus 100 will be described in brief below.

The X-ray CT apparatus has a rotary frame which is capable of rotating while supporting an X-ray tube configured to irradiate X-ray and an X-ray detector configured to detect the X-ray transmitted through a tested body at opposing positions. The X-ray CT apparatus is configured to collect projection data by rotating the rotary frame while radiating X-ray from the X-ray tube, and reconstruct X-ray CT images from the projection data. The X-ray CT image is a cross-sectional image on rotation planes (axial planes) between the X-ray tube and the X-ray detector. Here, the X-ray detector includes a plurality of detection element rows, which are X-ray detected elements arranged in a channel direction, arranged along the direction of body axis of the tested body. For example, the X-ray CT apparatus having the X-ray detector having sixteen detection element rows is configured to reconstruct a plurality of (sixteen, for example) X-ray CT images along the body axis of the tested body from the projection data collected by rotating the rotary frame by 360 degrees.

Also, for example, the X-ray CT apparatus is capable of rotating the rotary frame and reconstruct the 500 X-ray CT images covering the entire heart as volume data by helical scanning in which a table on which the tested body is placed is moved. Alternatively, for example, in the X-ray CT apparatus having the X-ray detector in which 320 detection element rows are arranged, the volume data covering the entire heart can be reconstructed only by performing conventional scanning in which the rotary frame is rotated by 360 degrees. Also, the X-ray CT apparatus is capable of photographing the X-ray CT images along the time series by continuously performing the helical scanning or the conventional scanning.

The MRI apparatus is capable of reconstituting an MRI image taken along an arbitrary one cross-section or MRI images (volume data) taken along plurality of arbitrary cross sections from MR signals collected by changing a phase-encoding gradient magnetic field, a slice-selecting gradient magnetic field, and a frequency-encoding gradient magnetic field. Also, the ultrasonic wave diagnostic apparatus is capable of creating an ultrasonic wave image taken along an arbitrary cross section by adjusting the position of an ultrasonic wave probe which performs two-dimensional scanning with the ultrasonic wave by the operator. Also, the ultrasonic wave diagnostic apparatus is capable of creating three-dimensional ultrasonic wave images (volume data) by performing the three-dimensional scanning with the ultrasonic wave by using a mechanical scanning probe or a 2D probe. In addition, the X-ray diagnostic apparatus creates two dimensional X-ray images by performing photographing in a state in which the position of a C-arm for supporting the X-ray tube and the X-ray detector is fixed. The X-ray diagnostic apparatus is capable of creating a three-dimensional X-ray image (volume data) by rotating the C-arm.

The image storing device 200 is a database for archiving medical images. Specifically, the image storing device 200 stores and archives medical images transmitted from the medical image diagnostic apparatus 100 in a storage of the own. The medical images archived in the image storing device 200 are archived in one-to-one correspondence with collateral information such as patient IDs, inspection IDs, apparatus IDs, and series IDs.

The medical image processing apparatus 30 corresponds to a work station or PC (Personal Computer) or the like used by doctors or laboratory personnel working in the hospital for interpreting medical images. The operator of the medical image processing apparatus 30 is capable of acquiring required medical images from the image storing device 200 by performing a search by using of the patient ID, the inspection ID, the apparatus ID, or the series ID. The medical image processing apparatus 30 according to the sixth embodiment is an apparatus configured to perform various types of image processing on the medical images in addition to displaying the medical images for interpretation. Specifically, the medical image processing apparatus 30 according to the sixth embodiment has a function to perform various types of image processing for supporting the image diagnosis.

The image processing system described above is not limited to the application in which the PACS is introduced. For example, the image processing system is also applied to a case where an electronic health record system which manages electronic health records attached with medical images is introduced. In this case, the image storing device 200 corresponds to a database configured to archive the electronic health records. Also, for example, the image processing system is applied in the same manner to a case where an HIS (Hospital Information System), an RIS (Radiology Information System) are introduced. The image processing system is not limited to an example of configuration described above. The functions of the respective apparatuses and the assignation thereof may be changed as needed according to the form of operation. Also, the medical image processing apparatus 30 may be applied to a case where the medical images are acquired directly from the medical image diagnostic apparatus 100 or a case where the medical images are acquired by using recording medium such as DVDs.

Then, the medical image processing apparatus 30 according to the sixth embodiment detects the myocardial boundary in input images scanned including the heart of the tested body as the image processing for supporting the image diagnosis. For example, the medical image processing apparatus 30 according to the sixth embodiment detects the myocardial boundary in the input images as medical images scanned including the heart of the tested body after having injected a contrast agent.

Here, the input images correspond to image data in which the shape of the heart and staining of respective regions due to the contrast agent is drawn in grayscale depending on the magnitude of the brightness value in a two-dimensional space or in a three-dimensional space. When performing a myocardial perfusion inspection, the input images corresponds to a plurality of angiographic image data along the time series scanned continuously. In the following description, a case where the myocardial boundary in the surround of the left ventricle in the cardiac cavity of the heart is detected, which is important when performing cardiac function analysis, will be described. In this case, the input image only has to be scanned after having injected the contrast agent and include at least part of the myocardium around the left ventricle.

Image processing to be performed by the medical image processing apparatus 30 according to the sixth embodiment will be described below with reference to FIG. 19 and so forth. FIG. 19 shows an example of a configuration of the medical image processing apparatus 30 according to the sixth embodiment. The medical image processing apparatus 30 according to the sixth embodiment includes an input unit 11, a display unit 12, a communicating unit 13, a storage unit 14, and a control unit 15 as shown in FIG. 19.

The input unit 11 is a mouse, a keyboard, a track ball, and the like, and receives inputs of respective operations with respect to the medical image processing apparatus 30 from the operator. Specifically, the input unit 11 according to the sixth embodiment receives the inputs of the information for acquiring the medical images to be subject to the image processing from the image storing device 200. For example, the input unit 11 receives inputs of the patient IDs, the inspection IDs, the apparatus IDs, the series IDs, and the like. Also, the input unit 11 according to the sixth embodiment receives inputs of conditions of the respective types of processing performed by the control unit 15 described later. The input unit 11 also functions as an acquiring unit for acquiring the three-dimensional volume data of the heart.

The display unit 12 is, for example, a monitor, and displays various items of information. Specifically, the display unit 12 according to the sixth embodiment displays GUI (Graphical User Interface) for receiving respective operations from the operator or the medical images.

The communicating unit 13 corresponds to an NIC (Network Interface Card) or the like and communicates with other apparatuses. For example, the communicating unit 13 transmits the information such as the patient ID which is received by the input unit 11 to the image storing device 200 and receives the medical images from the image storing device 200.

The storage unit 14 corresponds to a hard disk, a semiconductor memory element, and the like, and stores respective items of information. Specifically, the storage unit 14 according to the sixth embodiment stores information used for respective types of processing performed by the control unit 15 described later. More specifically, the storage unit 14 according to the sixth embodiment includes an image storage unit 141, a region-based temperate storage unit 142, a boundary pattern model storage unit 143, and a boundary model storage unit 144 as shown in FIG. 19.

The image storage unit 141 is configured to store the medical images acquired from the image storing device 200 via the communicating unit 13 or the result of processing of the control unit 15. More specifically, the image storage unit 141 is configured to store the input images acquired from the image storing device 200 as the object of detection of the myocardial boundary. For example, the image storage unit 141 is configured to store the 4 chamber View, the 3 chamber View, or the 2 chamber View enhanced with the contrast agent, or the volume data of the entire heart enhanced by the contrast agent, as the input image.

The region-based temperate storage unit 142 is configured to store the templates for detecting the respective regions of the heart by pattern matching in one-to-one correspondence with regions. The boundary pattern model storage unit 143 stores the boundary pattern model which is a pattern of the brightness values of the myocardium and the surround of the myocardial boundary of an image including the heart and enhanced by the contrast agent, and is modeled by learning. For example, the boundary pattern model storage unit 143 stores the boundary pattern model in which a pattern of the brightness values of the myocardium and the periphery of the myocardial boundary of the medical image including the heart enhanced by the contrast agent is modeled by learning. The boundary pattern model storage unit 144 stores the boundary model in which a myocardial boundary shape in the image used for learning the boundary pattern model is modeled by learning. For example, the boundary pattern model storage unit 144 stores the boundary model in which a myocardial boundary shape in the medical image used for learning the boundary pattern model is modeled by learning. For reference, a region-based temperate, the boundary pattern model, and the boundary model will be described later.

The control unit 15 corresponds to electronic circuits such as a CPU (Central Processing Unit) or the MPU (Micro Processing Unit) and integrated circuits such as an ASIC (Application Specific Integrated Circuit) or an FPGA (Field Programmable Gate Array), and performs a general control of the medical image processing apparatus 30.

For example, the control unit 15 according to the sixth embodiment controls a display of GUI or a display of the medical images for the display unit 12. Also, for example, the control unit 15 controls the transmission performed with respect to the image storing device 200 via the communicating unit 13. Also, for example, the control unit 15 controls storage or reading or the like of various data such as the medical image to the storage unit 14.

Also, for example, the control unit 15 performs various types of image processing with respect to the medical images. As an example of the image processing, the control unit 15 performs various types of rendering process for displaying the medical images as volume data on the display unit 12. The control unit 15 performs a volume rendering process for creating two-dimensional images reflecting the three-dimensional information of the volume data or a process for reconfiguring MPR images from the volume data by Multi Planer Reconstruction (MPR), as the rendering process.

Figure 20:
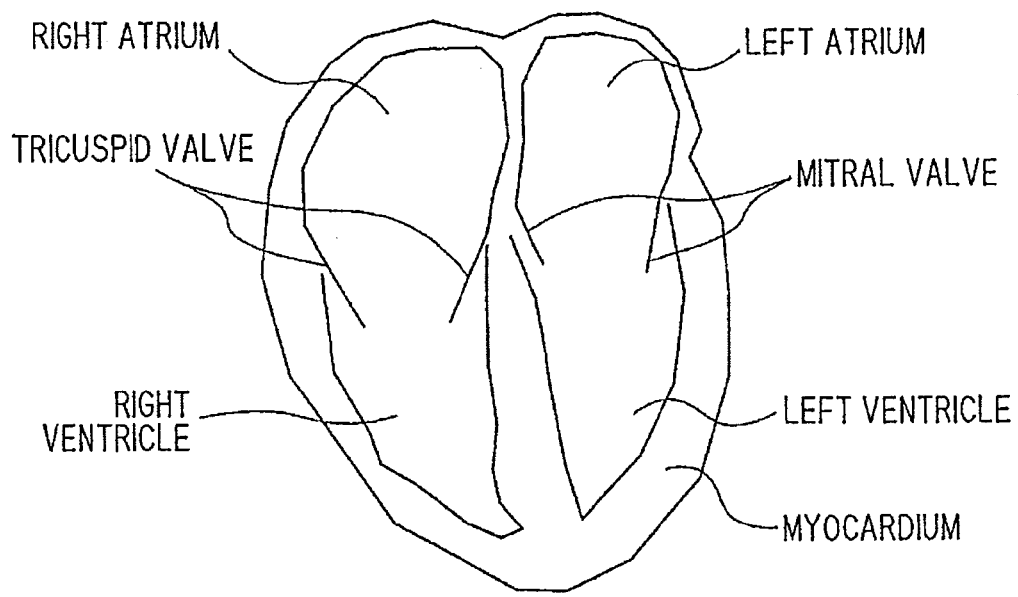
FIG. 20 is a drawing showing an example of an input image.

For example, in volume data, which is volume data scanned by the X-ray CT apparatus and includes the heart enhanced by the contrast agent, when the 4 chamber View of the heart is an object of the detection of the myocardial boundary, the input image is a cross-sectional image obtained by cutting the volume data with cross sections in which four chambers are included. Therefore, the operator inputs a display request of orthogonal three cross sections of the volume data (an axial plane, a coronal plane, and a sagittal plane) via the input unit 11. The control unit 15 creates orthogonal three cross sections from the volume data and displays the same on the display unit 12. The operator references the orthogonal three cross sections and sets a cross section in which all of cardiac cavities of a right atrium, a right ventricle, a left atrium and the left ventricle are included. The control unit 15 reconstructs the 4 chamber View (MPR image) by using the set cross section, and stores the reconstructed 4 chamber View into the image storage unit 141 as the input image. Here, the cross section set by the operator is, for example, a cross section parallel to the displayed coronal plane or an oblique cross section. FIG. 20 is a drawing showing an example of the input image.

The input image illustrated in FIG. 20 is a 4 chamber View of the heart in the volume data scanned by the X-ray CT image. As shown in FIG. 20, the input image includes the four cardiac cavities surrounded by the myocardium, that is, the right atrium, the right ventricle, the left atrium, and the left ventricle, and in addition, a tricuspid valve located at a boundary between the right atrium and the right ventricle and a mitral valve located between the left atrium and the left ventricle.

The control unit 15 according to the sixth embodiment includes a coordinate system detecting unit 151, a regional area detecting unit 152, a calculating unit 153, a correcting unit 154, and a boundary detecting unit 155 as shown in FIG. 19, and detects the myocardial boundary in the input image by the function of these processing units. For example, the control unit 15 according to the sixth embodiment detects the myocardial boundary in the surround of the left ventricle in the 4 chamber View as the input image shown in FIG. 20. In the following description, the boundary pattern model and the boundary model used in boundary detection will be described in detail, and then the process performed by the coordinate system detecting unit 151, the regional area detecting unit 152, the calculating unit 153, the correcting unit 154, and the boundary detecting unit 155 will be described in detail.

Figure 21:
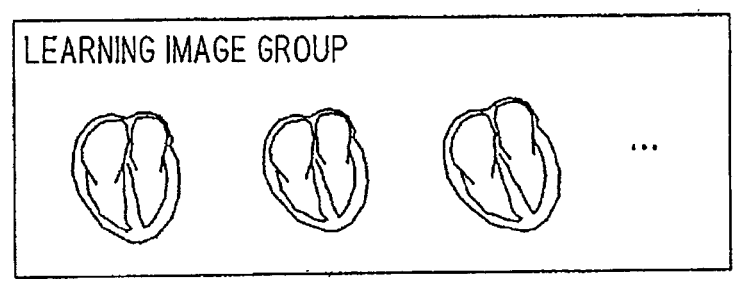
FIG. 21 is a drawing showing an example of a learning image group.

The boundary pattern model and the boundary model are created in advance by using the same learning image group for the boundary detection, and are stored in the spring 4. Specifically, the boundary model is created from the learning image group, and then the boundary pattern model is created by using the learning image group and the boundary model. For reference, in the embodiment, a case where the control unit 15 creates the boundary pattern model and the boundary model and stores the same in the storage unit 14 will be described. However, the embodiment may be a case where an apparatus other than the medical image processing apparatus 30 creates the boundary pattern model and the boundary model. In such a case, for example, the control unit 15 receives the boundary pattern model and the boundary model via the communicating unit 13 and stores the same in the storage unit 14. Alternatively, for example, the control unit 15 reads the boundary pattern model and the boundary pattern stored in the storage medium and stores the same into the storage unit 14. FIG. 21 is a drawing showing an example of the learning image group.

For example, the learning image group is the 4 chamber Views of the plurality of tested bodies scanned by contrast enhanced CT scans of the heart as shown in FIG. 21.

Figure 22A:
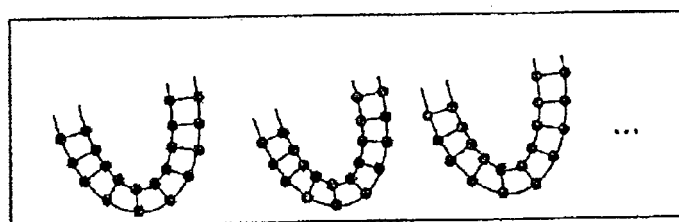
FIG. 22 is a drawing showing an example of creation of a boundary model.
Figure 22B:
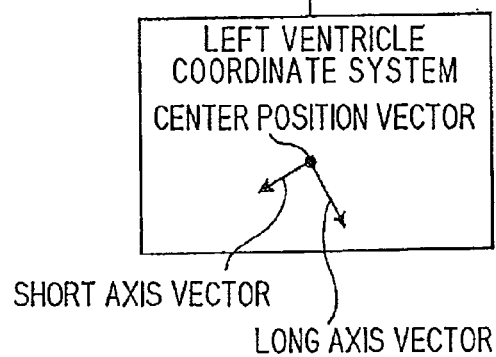
Figure 22C:
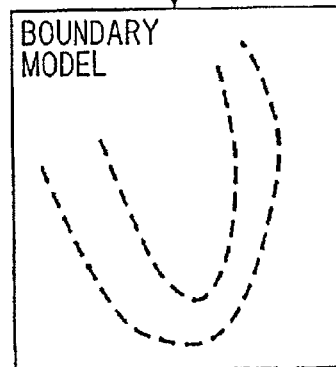

In such a case, the boundary pattern model according to the sixth embodiment is data of the pattern of the brightness values of the myocardium around the left ventricle and the surround of the myocardial boundary in the 4 chamber View group shown in FIG. 21 modeled by learning. Also, the boundary model according to the sixth embodiment is data of the shape of the myocardial boundary around the left ventricle in the 4 chamber View group shown in FIG. 21 modeled by learning. FIG. 22 is a drawing showing an example of creation of the boundary model, and FIG. 23 is a drawing showing an example of creation of the boundary pattern model.

For example, in the boundary model, two boundaries of the left ventricle with respect to the inner membrane and the outer membrane are both expressed as the myocardial boundary. Here, in the boundary model according to the sixth embodiment, since the learning image is the two-dimensional data, the respective boundaries are indicated by two-dimensional dot group. For example, a model creator sets pairs of a point on the inner membrane of the left ventricle and a point on the outer membrane of the left ventricle at respective 4 chamber Views which constitute the learning image group as shown in an upper drawing of FIG. 22, and sets a plurality of the pairs along the myocardium. Assuming the number of pairs set on the respective learning images to be "N", the inner membrane shape of the left ventricle of each of the learning images is expressed by "N" vectors, and the outer membrane shape of the left ventricle of each of the learning images is expressed by "N" vectors. In other words, "2N" vectors for each of the learning images constitute the boundary vector group for learning the boundary shape.

However, as shown in FIG. 21, the sizes and the directions of the respective 4 chamber Views which constitute the learning image group are different. Therefore, the shapes expressed by the respective boundary vector groups are expressed by different image coordinate systems, respectively. Therefore, in creation of the boundary model, normalization of the shapes by using the left ventricle coordinate systems obtained from the respective learning images is performed.

When creating the boundary model, the control unit 15 obtains a long axis of the left ventricle, and a center of the left ventricle and the short axis orthogonal to the long axis from each of the learning images. For example, the control unit 15 sets a segment connecting the position of the mitral valve and the cardiac apex of the left ventricle as a long axis and sets the center point of such a segment as a center position of the left ventricle. Then, the control unit 15 sets a direction orthogonal to the direction of the long axis and directed toward the right ventricle as a short axis direction. Accordingly, in each of the learning images, the orthogonal coordinate system of the left ventricle defined by a center position vector, a long axis vector having an original position at the center position, and a short axis vector is obtained as shown in a lower left drawing of FIG. 22. Then, the control unit 15 obtains a normalization orthogonal coordinate system by setting the scale of the left ventricle coordinate system obtained by each of the learned images in such a manner that the length from the center position of the left ventricle to the cardiac apex of the left ventricle to be "1". Then, the control unit 15 converts the coordinate system of the boundary vector group on the basis of the normalization orthogonal coordinate system for each of the learned images. Accordingly, the control unit 15 obtains a learned boundary vector group normalized by the normalization orthogonal coordinate system.

Then, the control unit 15 obtains an average shape and a shape base vector for expressing an arbitrary shape by a shape model on the basis of "Active Shape Model", which is a statistic shape learning method, for example, from the learning boundary vector group. The control unit 15 stores the average shape and the shape base vector in the boundary model storage unit 144 as the boundary model. For example, the average shape as the boundary model becomes a vector group which expresses an average shape of the inner membrane shape and the outer membrane shape of the left ventricle as indicated by two dot lines in a lower right drawing in FIG. 22.

In the shape model on the basis of the "Active Shape Model", an arbitrary shape "x" can be created by the following expression (2), where "x bar" is the average shape, "φ" is the shape base vector, and "b" is a weighting coefficient,

[Expression 2]

$$x = \bar{x} + \Phi b \tag{2}$$

When creating the boundary pattern model, the control unit 15 performs extraction of the brightness value profiles on the segments passing through the inner membrane boundary points and the outer membrane boundary points set as pairs on each of the learning images. The control unit 15 extracts a plurality of brightness value profiles from one learning image because a plurality of the pairs of the inner membrane boundary points and the outer membrane boundary points are set. Then, the control unit 15 performs the pattern learning of the brightness values by using a plurality of the brightness value profiles extracted from each of the learning image. For example, the control unit 15 performs extraction of the brightness value profiles by using pairs of two points (the inner membrane boundary point and the outer membrane boundary point) set for the learning images shown on an upper drawing in FIG. 22.

The segments used for the brightness value profiles are set, for example, as shown in an upper left drawing in FIG. 23. First of all, the control unit 15 sets a straight line which is extended from a segment connecting the inner membrane boundary point and the outer membrane boundary point inward (toward the left ventricle cavity) and outward (toward the outside of the left ventricle). Then, the control unit 15 sets a point located inside by the same distance as the distance between the inner and outer membranes (inner point) and a point located outside by the same distance as the distance between the inner and outer membranes (outer pint) on the set straight line. Then, the control unit 15 extracts the brightness value profile on the segment connecting the inner point and the outer point as shown in the upper left drawing in FIG. 23. Here, as shown in the upper left drawing in FIG. 23, a portion between the inner point and the inner membrane boundary point corresponds to the left ventricle cavity, and a portion between the inner membrane boundary point and the outer membrane boundary point corresponds to the myocardium, a portion between the outer membrane boundary point and the outer point corresponds to the outside of the left ventricle. The control unit 15 extracts the brightness value profile, for example, in a direction from the inner point toward the outer point.

Here, the control unit 15 sets a plurality of segments connecting the inner points and the outer points in one learning image. Accordingly, the control unit 15 acquires the brightness values within a range surrounded by two dashed lines shown in upper right drawing in FIG. 23 as a brightness value pattern in the peripheral area of the myocardial boundary. Then, the control unit 15 creates the boundary pattern model by learning the brightness value patterns in the peripheral area of the myocardial boundaries of the respective learning images.

For example, the control unit 15 specifies corresponding pairs among the learning images by converting the left ventricle coordinate systems of the respective learning images into the normalization orthogonal coordinate system. Then, for example, the control unit 15 calculates an average value of the brightness value profiles between the specified pairs to create the boundary pattern model. Alternatively, the control unit 15 calculates the average values and the standard deviation of the brightness value profiles as the boundary pattern model.

A lower drawing in FIG. 23 shows an example of the boundary pattern model created by the process described above. The boundary pattern model has a brightness value row in which the brightness values of the pixels are arranged in the direction from the left ventricle cavity through the myocardium to the outside of the left ventricle by pair (P). Also, the control unit 15 indexes the regions where the pixels of the respective brightness values "the left ventricle cavity, the myocardium, and the outside of the left ventricle" in one-to-one correspondence in the brightness value row. Also, for example, the control unit 15 arranges the brightness value row (the pairs) in "the order from side wall, cardiac apex, toward septula".

Accordingly, for example, the boundary pattern model stores brightness values "a1 to a10" of ten pixels which constitute the left ventricle cavity, brightness values "a11 to a20" of ten pixels which constitute the myocardium, brightness values "a21 to a30" of ten pixels which constitute the outside of the left ventricle as a brightness value row of "P:1" as shown in the lower drawing in FIG. 23. For reference, in the boundary pattern model, whether the region on the outside of the left ventricle is outside of the heart or the right ventricle cavity may also be indexed as shown in the lower drawing in FIG. 23. In the example shown in the lower drawing in FIG. 23, the brightness values "a21 to a30" of the ten pixels which constitute the outside of the left ventricle is indexed as the "outside of the heart".

Also, since the distance between the inner and outer membranes is not uniform, the length of the brightness value rows varies from pair (P) to pair (P). For example, the boundary pattern model stores brightness values of thirteen pixels which constitute the left ventricle cavity, brightness values of thirteen pixels which constitute the myocardium, brightness values of thirteen pixels which constitute the outside of the left ventricle as a brightness value row of "P:200". Alternatively, the length of the brightness value row may be fixed and the intervals between the pixels to be acquired for creating the brightness value rows may be differentiated depending on the distance between the inner and outer membranes. In such a case, for example, the numbers of pixels which constitute the respective brightness value rows between "P:1" and "P:2" are the same, and the intervals at which the brightness values "a1" and "a2" of "P:1" are acquired and the intervals at which the brightness values "a31" and "a32" of "P:2" are acquired are different. The control unit 15 stores the boundary pattern model exemplified in the lower drawing in FIG. 23 in the boundary pattern model storage unit 143. The control unit 15 is capable of acquiring information such that the first pixel in the brightness value row of "P:1" is a pixel in the area of the left ventricle having the brightness value of "a1", and the fifteenth pixel is a pixel in the myocardial area having the brightness value of "a15" from the boundary pattern model in the downstream process.

Then, the coordinate system detecting unit 151, the regional area detecting unit 152, the calculating unit 153, the correcting unit 154, and the boundary detecting unit 155 as shown in FIG. 19 detect the myocardial boundary in the input image by using the boundary pattern model and the boundary model stored in advance. First of all, the coordinate system detecting unit 151 detects at least the long axis of the heart as the left ventricle coordinate system indicating the position and posture of the heart in the input image from the input image. In the sixth embodiment, the coordinate system detecting unit 151 detects at least the long axis of the left ventricle as the left ventricle coordinate system from the input image. Also, in the sixth embodiment, the coordinate system detecting unit 151 detects the short axis of the heart in the input image as the left ventricle coordinate system together with the long axis.

Subsequently, an information detecting method to be performed by the coordinate system detecting unit 151 will be described by dividing roughly into two methods of first information detecting method and a second information detecting method. When performing the first information detecting method, the coordinate system detecting unit 151 detects the position of the mitral valve and the position of the cardiac apex from the input image, and a midpoint of the segment connecting the position of the mitral valve and the position of the cardiac apex is determined to be a center position of the left ventricle. Then, the coordinate system detecting unit 151 detects the vector from the center position of the left ventricle to the position of the cardiac apex as a long axis. Specifically, the coordinate system detecting unit 151 uses templates for regions for pattern matching stored in the above-described region-based temperate storage unit 142 in advance.

Figure 24:
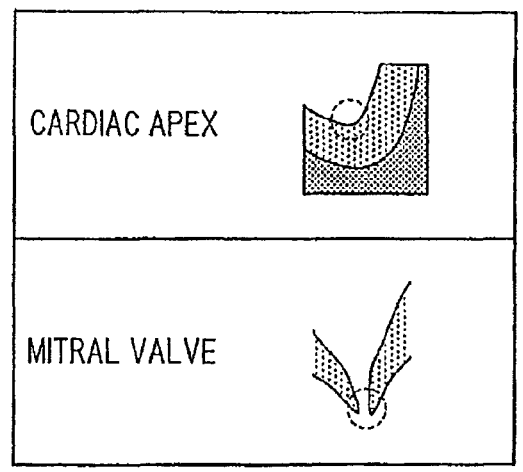
FIG. 24 is a drawing showing an example of a region-based template.

FIG. 24 is a drawing showing an example of a region-based template. For example, the region-based temperate storage unit 142 stores the brightness pattern in the surround of the cardiac apex (see dotted circle in the drawing) learned in advance as shown in FIG. 24 as a cardiac apex template. Also, for example, the region-based temperate storage unit 142 stores the brightness pattern in the surround of the mitral valve (see dotted circle in the drawing) learned in advance as shown in FIG. 24 as a mitral valve template.

Figure 25:
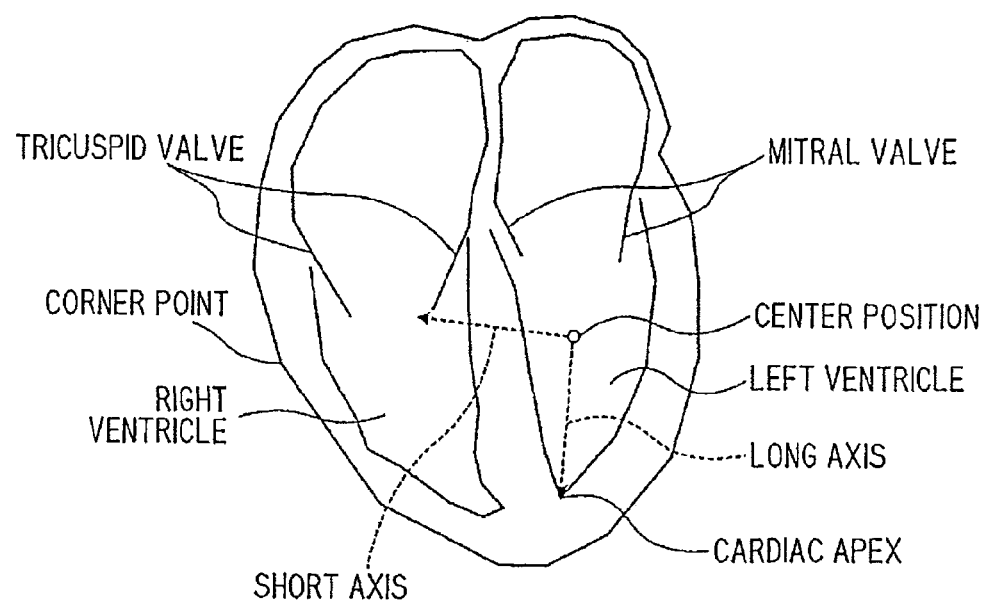
FIG. 25 is an example of a left ventricle coordinate system.

The coordinate system detecting unit 151 detects the position of the mitral valve by performing the pattern matching between the input image and the mitral valve template. In the same manner, the coordinate system detecting unit 151 detects the position of the cardiac apex by performing the pattern matching between the input image and the cardiac apex template. FIG. 25 is a drawing showing an example of the left ventricle coordinate system. As shown in FIG. 25, the coordinate system detecting unit 151 detects the center position and the long axis of the left ventricle as the left ventricle coordinate system. Accordingly, the coordinate system detecting unit 151 detects the original point and the long axis vector in the left ventricle coordinate system of the input image.

Figure 26:
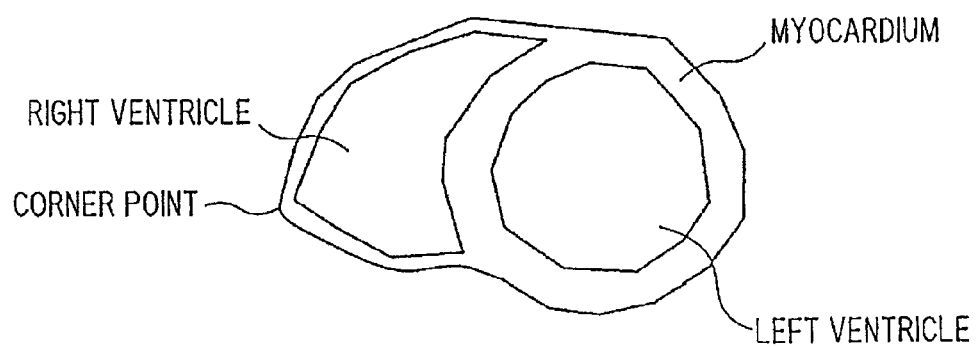
FIG. 26 is a drawing showing an example of a region used for short axis detection.

Also, when performing the first information detecting method, the coordinate system detecting unit 151 further detects a short axis in the 4 chamber View as an input image. Specifically, the coordinate system detecting unit 151 uses a region-based template in the same manner as the detection of the long axis. For example, the coordinate system detecting unit 151 uses a right ventricle corner point temperate of the right ventricle as the region-based template. FIG. 26 is a drawing showing an example of a region used for short axis detection. Here, the corner point of the right ventricle means specifically a point located on the outermost side in the outer surround of the right ventricle in the 2 chamber View in which the left ventricle and the right ventricle are included as illustrated in FIG. 26. The coordinate system detecting unit 151 detects the position of the corner point of the right ventricle by performing the pattern matching between the input image and the corner point template. The coordinate system detecting unit 151 obtains a segment orthogonal to the long axis from the corner point of the right ventricle, and moves the obtained segment to the original point in parallel to set a short axis as shown in FIG. 25. Accordingly, the coordinate system detecting unit 151 detects the short axis vector in the left ventricle coordinate system of the input image.

When detecting the short axis of the 4 chamber View in the first information detecting method, the coordinate system detecting unit 151 may detect the position of the tricuspid valve by using a tricuspid valve template in addition to the corner point of the right ventricle. When detecting the short axis of the 3 chamber View in the first information detecting method, the coordinate system detecting unit 151 detects the left ventricle outflow tract which allows blood to flow from the left ventricle to a large artery. Also, when detecting the short axis of the 2 chamber View in the first information detecting method, the coordinate system detecting unit 151 detects a front wall point.

In contrast, when detecting the long axis in the second information detecting method, the coordinate system detecting unit 151 detects the long axis by performing the pattern matching between the long axis template as a brightness pattern in the surround of the long axis learned in advance and the input image. The "surround of the long axis" described above indicates a rectangular area uniquely determined from the long axis. Also, when detecting the short axis in the second information detecting method, the coordinate system detecting unit 151 detects a short axis by performing the pattern matching between the short axis template as a brightness pattern in the surround of the short axis learned in advance and the input image.

The sixth embodiment may be a case where the long axis and the short axis are detected as the left ventricle coordinate system by a method other than those described above. Also, the sixth embodiment may be a case where only the information of the long axis is detected as the left ventricle coordinate system. The method of detecting the left ventricle coordinate system is not limited to the methods described above, and arbitrary methods may be used.

Then, the regional area detecting unit 152 detects the predetermined regional area in the input image by using the left ventricle coordinate system. More specifically, the regional area detecting unit 152 detects an area including at least one of the ventricles, the atriums, the left ventricle outflow tract, a valve ring, a papillary muscle, the myocardium, and a coronary artery as a predetermined regional area. Furthermore, in the sixth embodiment, the regional area detecting unit 152 detects a plurality of regional areas by using the left ventricle coordinate system. In the sixth embodiment, a case where the regional area detecting unit 152 detects the left ventricle area (the left ventricle cavity area), the myocardial area, and the right ventricle area (the right ventricle cavity area) will be described using the left ventricle coordinate system. The regional area includes at least one pixel. FIG. 27 to FIG. 31 are drawings showing a method of detecting the regional area.

Figure 27:
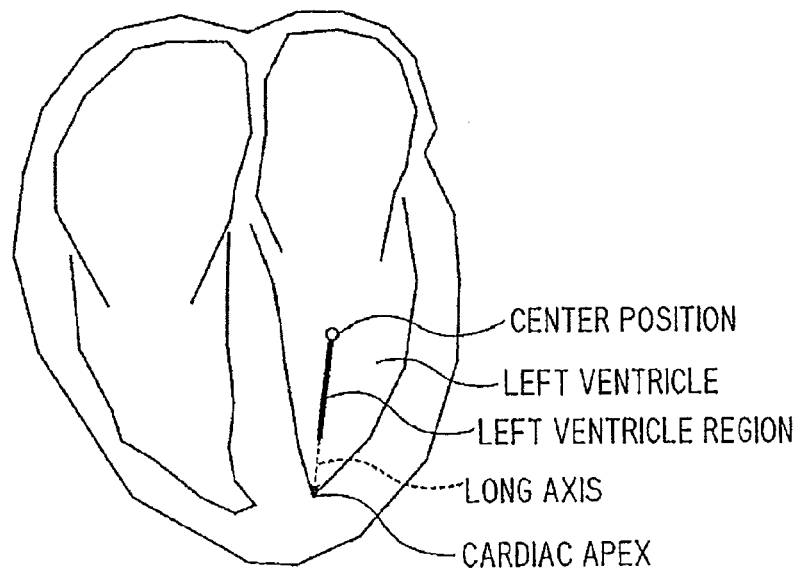
FIG. 27 is a drawing (1) showing a method of detecting a regional area.
Figure 28:
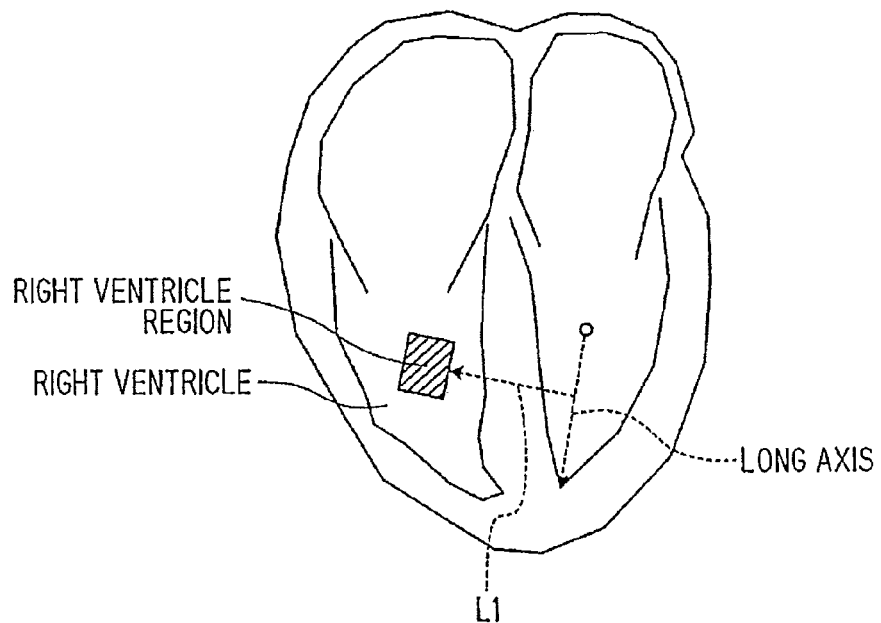
FIG. 28 is a drawing (2) showing a method of detecting a regional area.
Figure 29:
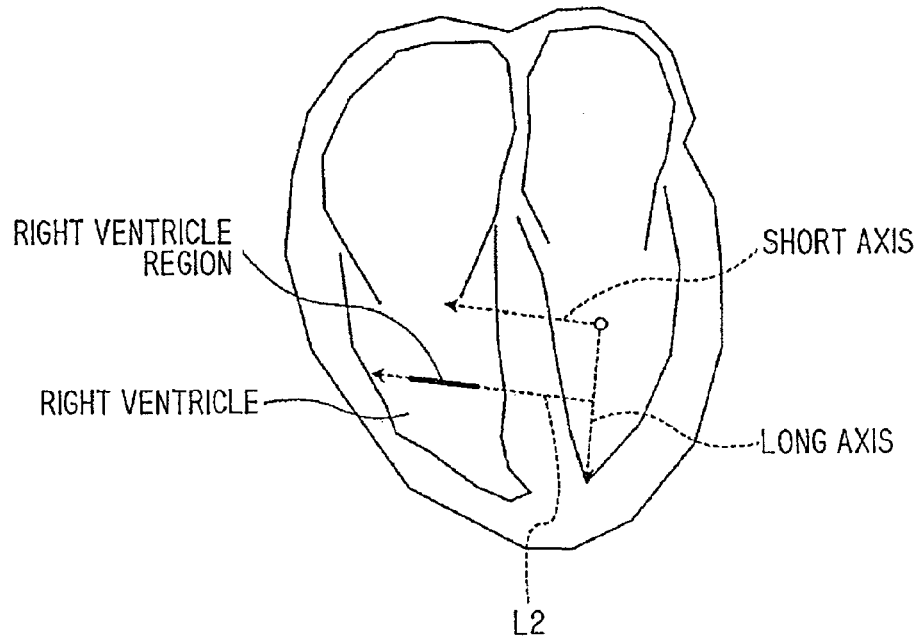
FIG. 29 is a drawing (3) showing a method of detecting a regional area.
Figure 30:
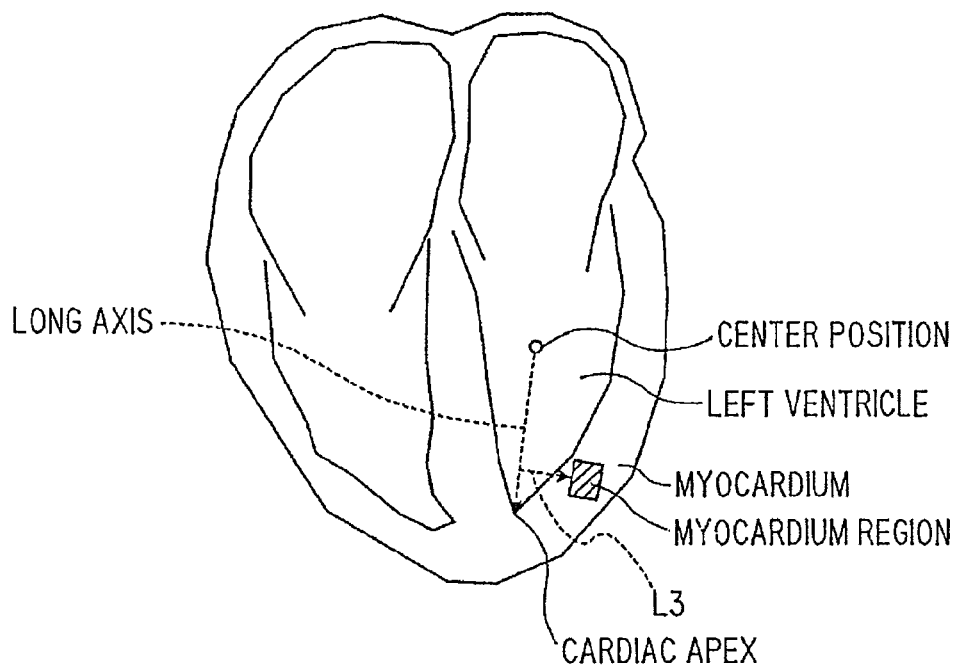
FIG. 30 is a drawing (4) showing a method of detecting a regional area.

First of all, the regional area detecting unit 152 detects a predetermined range determined by the long axis included in the left ventricle coordinate system as the regional area in the input image. In the detection of the left ventricle area, for example, as shown in FIG. 27, the regional area detecting unit 152 detects a partial range of the long axis as the left ventricle area. In the method exemplified in FIG. 27, the regional area detecting unit 152 detects a solid line portion on the long axis as the left ventricle area. Alternatively, the regional area detecting unit 152 detects a rectangle of a predetermined size including the long axis as the left ventricle area. The partial range on the long axis and the size of the rectangle described above are values which can be obtained statistically, and these values are set to the regional area detecting unit 152 in advance.

For detection of the right ventricle, there are a first detecting method by using the long axis and a second detecting method by using the long axis and the short axis. In the first detecting method for the right ventricle area, the regional area detecting unit 152 detects, for example, an area within a predetermined range located at a predetermined distance from the long axis indicated by a hatched portion in FIG. 28 as a right ventricle area. In the method exemplified in FIG. 28, a "vector L1" having a start point at a midpoint of the segment between the center of the left ventricle and the cardiac apex and a terminal point located at a predetermined distance leftward from the midpoint on the image is set. In the method exemplified in FIG. 28, the "vector L1" corresponds to a vector orthogonal to the long axis. Then, for example, the regional area detecting unit 152 detects a rectangle having a predetermined size having two segments orthogonal to the "vector L1" as long sides and two segments parallel to the "vector L1" as short sides with reference to the terminal point of the "vector L1" as the left ventricle area. For reference, the values of the distance from the midpoint to the terminal point and the size of the rectangle are values which can be obtained statistically, and these values are set to the regional area detecting unit 152 in advance. Also, the left-and-right direction in the input image may be acquired from information such as the coordinate system of the medical image diagnostic apparatus 100 and the body position of the tested body provided as additional information on the medial image in conformity to DICOM standard.

The second detecting method for the right ventricle area is performed in a case where the information relating to the short axis is detected as the left ventricle coordinate system. In other words, in the second detecting method, the regional area detecting unit 152 detects a predetermined range determined by the direction of the long axis and the direction of the short axis as a regional area (the right ventricle area) in the input image. For example, in the second detecting method of the right ventricle area, the regional area detecting unit 152 detects a segment on a "vector L2" parallel to the short axis vector and having a start point at a midpoint of the segment between the center of the left ventricle and the cardiac apex as the right ventricle area as indicated by a solid line in FIG. 29. Alternatively, the regional area detecting unit 152 detects a rectangle of a predetermined size including the "vector L2" as the right ventricle area. For reference, the position of the start point of the "vector L2", the position and the length of the segment on the "vector L2", and the size of the rectangle are values which can be obtained statistically, and these values are set to the regional area detecting unit 152 in advance.

For detection of the myocardial area, a first detecting method by using the long axis and a second detecting method by using the boundary model described above exist. In the first detecting method for the myocardial area, the regional area detecting unit 152 detects, for example, an area having a predetermined size located at a predetermined distance from the long axis indicated by a hatched rectangle in FIG. 30 as the myocardial area. In the method exemplified in FIG. 30, a "vector L3" having a start point at a point located at a predetermined distance from the center of the left ventricle on the long axis and a terminal point located at a predetermined distance rightward from the start point on the image is set. In the method exemplified in FIG. 30, the "vector L3" corresponds to a vector orthogonal to the long axis. Then, for example, the regional area detecting unit 152 detects a rectangle having a predetermined size having two segments orthogonal to the "vector L3" as long sides and two segments parallel to the "vector L3" as short sides with reference to the terminal point of the "vector L3", as the myocardial area. The positions of the start point and the terminal point and the size of the rectangle are values which can be obtained statistically, and these values are set to the regional area detecting unit 152 in advance. The left-and-right direction in the input image can be acquired from the additional information of the medical image as described above.

Figure 31:
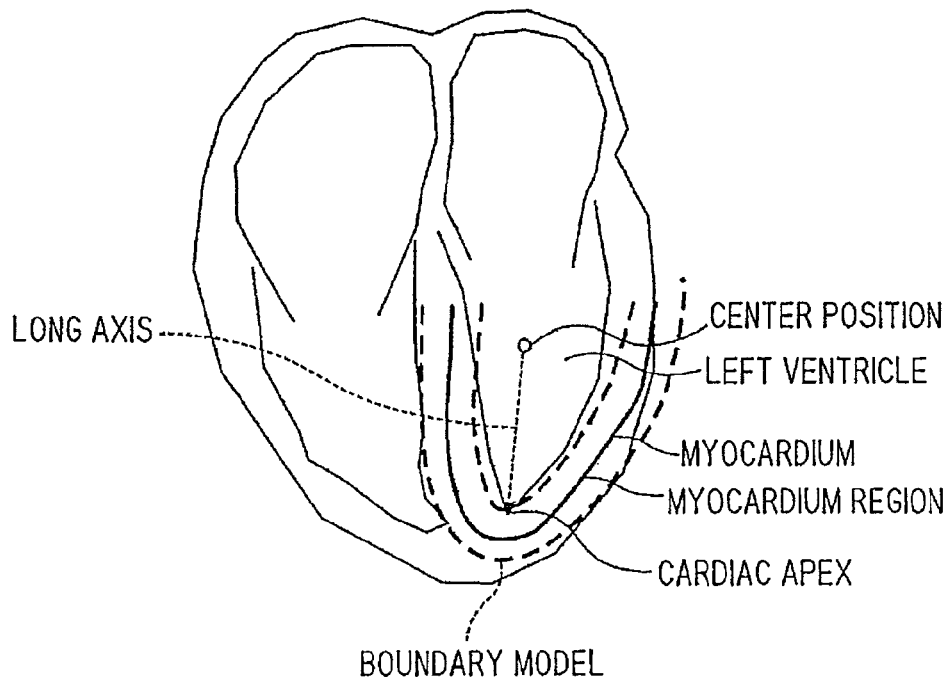
FIG. 31 is a drawing (5) showing a method of detecting a regional area.

Also, in the second detecting method for the myocardial area, the regional area detecting unit 152 converts the boundary model (average shape) indicated by two dot lines in FIG. 31 into the left ventricle coordinate system of the input image. Then, the regional area detecting unit 152 applies the boundary model after the conversion to the input image on the basis of the left ventricle coordinate system (the position of the center of the left ventricle and the position of the cardiac apex). The boundary model has, for example, a bowl shape about the long axis, and may be applied uniquely by using the information of the long axis of the input image and the information of the long axis of the boundary model after the conversion. Then, the regional area detecting unit 152 obtains a centerline (see a solid curved line in FIG. 31) of the applied boundary model and detects part of the centerline as the myocardial area. The myocardial area determined by the above-described process is a roughly defined area, and the sixth embodiment may be a case where the rectangle or the like in the applied boundary model is detected in addition to the centerline as the myocardial area. Also, when performing the second detecting method for the myocardial area, a case where the regional area detecting unit 152 detects the myocardial area from the result of processing in the course of the application process of the boundary model to be executed repeatedly by the boundary detecting unit 155 on the downstream step is also applicable.

Also, for example, when a plurality of the boundary models are stored, the regional area detecting unit 152 may select a boundary model most matching the left ventricle coordinate system of the input image from among the plurality of boundary models and detect the myocardial area by using the selected boundary model.

As a third detecting method for the myocardial area, a case where the regional area detecting unit 152 uses the information of the short axis is also applicable. For example, a case where the regional area detecting unit 152 detects a predetermined range which is considered to be the myocardium statistically on the straight line parallel to the short axis vector as the myocardial area is also applicable.

Also, the method of detecting the regional area is not limited to the methods described above, and arbitrary methods may be used as long as the method is capable of specifying the regional area by using the left ventricle coordinate system.

Then, the calculating unit 153 calculates the degrees of staining indicating the concentration of the contrast agent of the predetermined rational area on the basis of the left ventricle coordinate system. In the sixth embodiment, the calculating unit 153 performs a degree-of-staining calculating process by using the regional area detected by the regional area detecting unit 152. For reference, the sixth embodiment may be a case where the process of the regional area detecting unit 152 is not performed but the process of the calculating unit 153 is performed because the left ventricle area is uniquely specified from the long axis, for example.

In the input image, the concentration of the contrast agent has a correlation with the brightness value and, for example, the brightness value is increased with increase in concentration of the contrast agent, so that the degree of staining may be calculated from the brightness value in the input image.

Therefore, the calculating unit 153 calculates a statistic representative value in the brightness value row of a plurality of pixels which constitute the regional area as a degree of staining in the regional area. For example, the calculating unit 153 sets the brightness values of all the pixels which constitute the regional area as a brightness value row. Alternatively, for example, the calculating unit 153 selects a predetermined number of pixels from among all the pixels which constitute the regional area at random and sets the brightness values of the selected plurality of the pixels as the brightness value row. Then, the calculating unit 153 employs a median value of the brightness value row as a degree of staining.

For reference, the statistic representative value is not limited to the median value, and may be values such as a most frequent value, a maximum value, a minimum value, an average value, or a standard variation. A case where the representative value employed as the degree of staining is a value obtained by sorting the brightness value row in the order of the brightness values and calculated as a top $N^{th}$ value in the sorted brightness value row is also applicable. Also, the representative value employed as the degree of staining may be a combination of a plurality of the representative values such as the average value and the standard variation.

Then, the correcting unit 154 performs a correction to cause the brightness values of the input image and the brightness values of the boundary pattern model to go close in a regional area by using the degree of staining of the corresponding regional area. Specifically, the correcting unit 154 according to the sixth embodiment performs the correcting process by using the degree of staining with respect to the boundary pattern model and creates the correction boundary pattern model. More specifically, the correcting unit 154 according to the sixth embodiment performs correction for causing the brightness values of the boundary pattern model in a regional area to go close to the brightness values of the input image of the corresponding regional area on the basis of the degree of staining of the regional area, and creates the correction boundary pattern model.

Methods of correcting the boundary pattern model are different for each of the regional areas of an object to be corrected. The method of correcting the boundary pattern model will be described below in the order of the left ventricle area, the right ventricle area, and the myocardial area. FIG. 32 is a drawing for explaining a correcting process according to the sixth embodiment. The following are description on the assumption that the brightness value of the "$i^{th}$" pixel of the boundary pattern model is "ai", and the value obtained by correcting "ai" by the correcting unit 154 is "pi".

First of all, when the "$i^{th}$" pixel in the boundary pattern model is a pixel of the left ventricle cavity, the correcting unit 154 calculates "pi" with, for example, the following expression (3).

[Expression 3]

$$p_i = a_n + \frac{d_l - a_n}{a_l - a_n}(a_i - a_n) \quad (3)$$

Here, in the expression (3), "dl" is the degree of staining of the left ventricle area. Also, "al" is a representative value of the brightness values of all the pixels (for example, an average value) indexed as the left ventricle cavity in the same brightness value row as "ai" in the boundary pattern model. Also, "an" is a brightness value of a pixel indexed as the inner membrane boundary point in the myocardium in the brightness value row of the same pair as "ai" as shown in (A) in FIG. 32. For reference, the correcting unit 154 is capable of acquiring "an" with a first pixel in the pixels indexed as the myocardium in the brightness value row of the same pair as "ai" as the inner membrane boundary point.

Figure 32A:
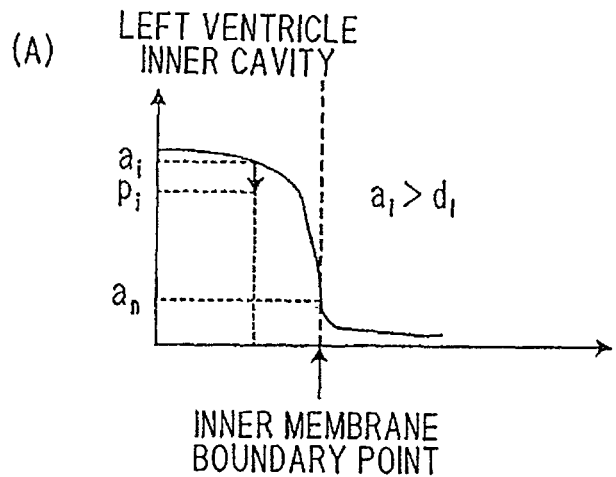
FIG. 32 is a drawing for explaining a correcting process according to a sixth embodiment.

For example, as shown in FIG. 32(A), when "ai" is larger than "dl", the correcting unit 154 performs an arithmetic process with the expression (3), thereby calculating "pi" which is a value reduced from the value of "ai" so that the "ai" becomes a value close to "dl" with reference to "an".

Also, when the "$i^{th}$" pixel of the boundary pattern model is the outside of the left ventricle and is the pixel of the right ventricle cavity, the correcting unit 154 calculates "pi" with the following expression (4).

[Expression 4]

$$p_i = a_p + \frac{d_r - a_p}{a_r - a_p}(a_i - a_p) \quad (4)$$

Figure 32B:
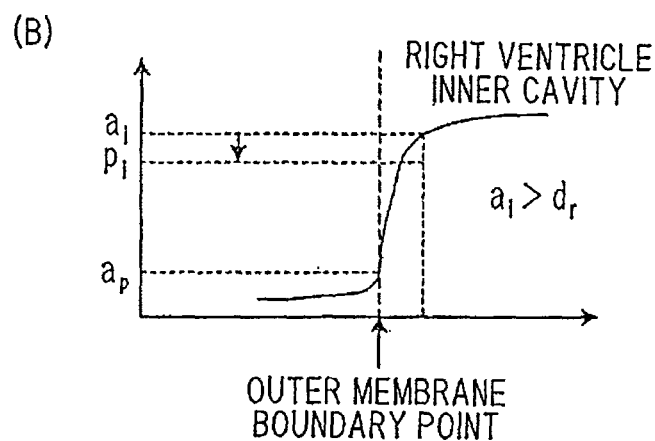

Here, in the expression (4), "dr" is the degree of staining of the right ventricle area. Also, "ar" is a representative value of the brightness values of all the pixels (for example, an average value) indexed as the right ventricle cavity in the same brightness value row as "ai" in the boundary pattern model. Also, "ap" is a brightness value of a pixel indexed as the outer membrane boundary point in the myocardium in the brightness value row of the same pair as "ai" as shown in FIG. 32(B). For reference, the correcting unit 154 is capable of acquiring "ap" with the last pixel in the pixels indexed as the myocardium in the brightness value row of the same pair as "ai" as the outer membrane boundary point.

For example, as shown in FIG. 32(B), when "ai" is larger than "dr", the correcting unit 154 performs an arithmetic process with the expression (4), thereby calculating "pi" which is a value reduced from the value of "ai" so that the "ai" becomes a value close to "dr" with reference to "ap". For reference, when whether the region of the outside of the left ventricle is the outside of the heart or in the right ventricle cavity is not indexed in the boundary pattern model, the correcting unit 154 compares the brightness value of "ai" and a threshold value, thereby determining whether the "$i^{th}$" pixel is a pixel of the outside of the heart or the pixel in the right ventricle cavity. Here, the threshold value is a statistically obtained value.

Also, when the "$i^{th}$" pixel of the boundary pattern model is the pixel of the myocardium, the correcting unit 154 calculates "pi" with the following expression (5), for example.

[Expression 5]

$$p_i = a_i - a_m + d_m \quad (5)$$

Here, in the expression (5), "dm" is the degree of staining of the myocardial area. Also, "am" is a representative value of the brightness values of all the pixels (for example, an average value) indexed as the myocardium in the same brightness value row as "ai" in the boundary pattern model.

Figure 32C:
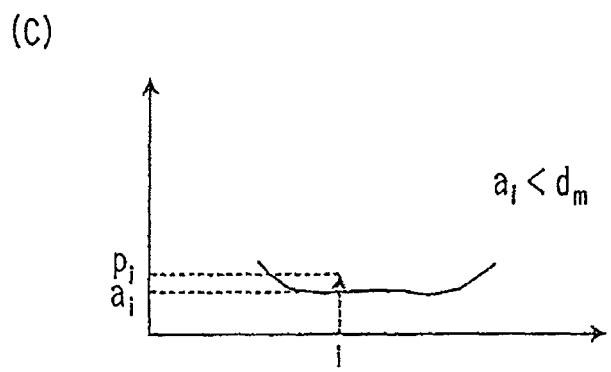

For example, as shown in FIG. 32(C), when "ai" is smaller than "dm", the correcting unit 154 performs an arithmetic process with the expression (5), thereby calculating "pi" which is a value increased from the value of "ai" so that the "ai" becomes a value close to "dm".

Figure 35:
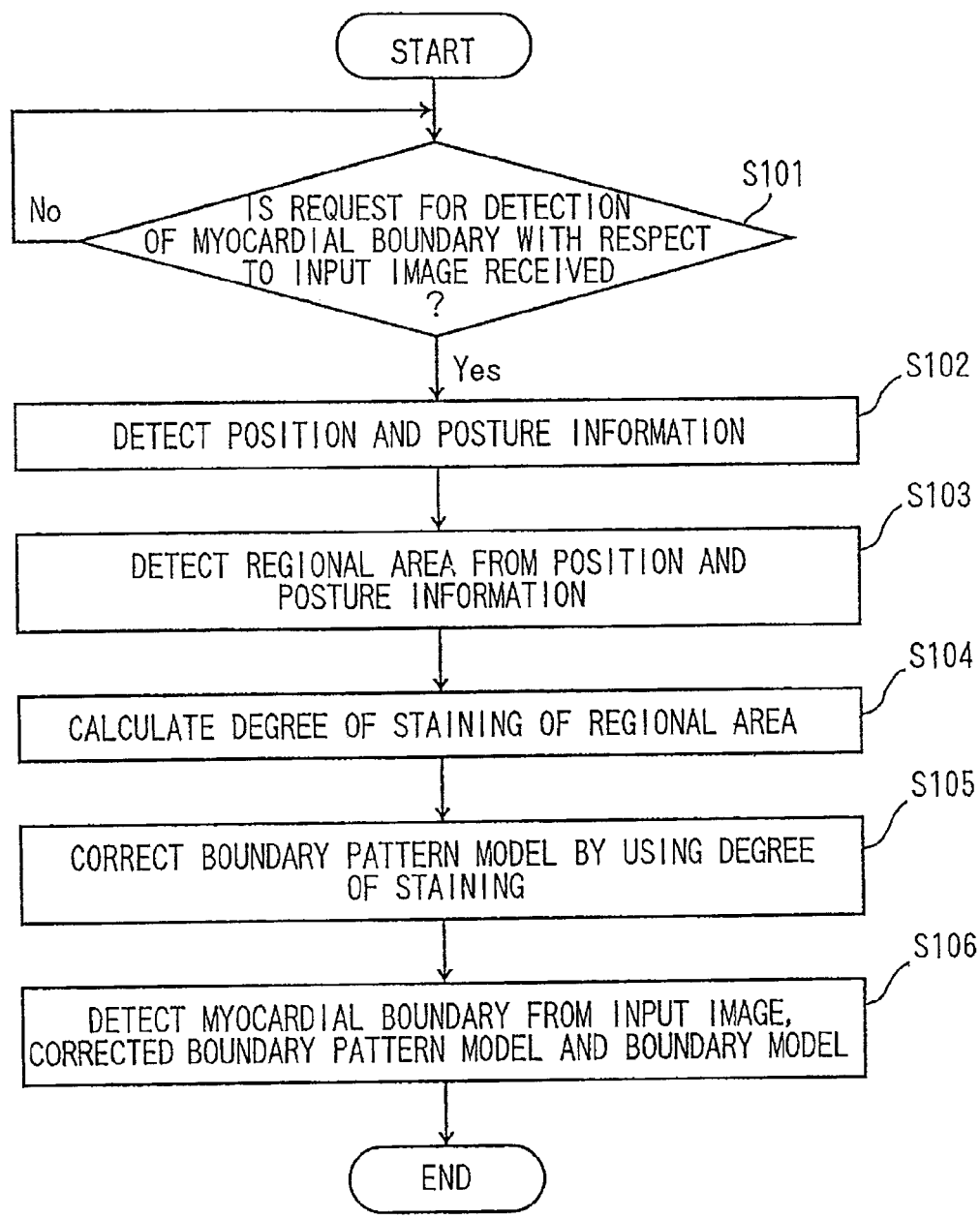
FIG. 35 is a flowchart showing an example of a process of a medical image processing apparatus according to a sixth embodiment.

The correcting unit 154 creates a corrected boundary pattern model by the arithmetic process with the expressions (3) to (4). FIG. 35 is a drawing showing an example of correction of a boundary pattern model. The brightness value profile exemplified in FIG. 35 is a brightness value profile from a pixel of the left ventricle cavity toward a pixel of the right ventricle cavity, and is a plot of the brightness values in the surround of the septula which is the myocardium around the left ventricle. An example shown in FIG. 35 shows that the brightness values of the brightness value profile of the boundary pattern model before correction are larger than the brightness value profile of the boundary pattern model after the correction in the left ventricle, the myocardium, and the right ventricle, respectively. This indicates that the degree of staining of the input image is higher than the degree of staining of the learning image group.

For reference, in the method of correcting the boundary pattern model described above, a case where the brightness values of the boundary pattern model are subjected to a rounding process on the basis of the degree of staining is also applicable. Also, the method of correcting the boundary pattern model is not limited to the arithmetic process on the basis of the above described expression (3) to the expression (5). As long as the correction to cause the brightness values of the boundary pattern model to go close to the brightness values of the input image is enabled by performing the correcting process by using the degree of staining by a combination of an adding process, a subtracting process, a multiplying process, a dividing process, or a rounding process, the correcting unit 154 may perform an arbitrary arithmetic process.

Then, the boundary detecting unit 155 detects the boundary of the myocardium in the input image by using the data after the correction by the correcting unit 154. In other words, the boundary detecting unit 155 according to the sixth embodiment detects the boundary of the myocardium in the input image by using the corrected boundary pattern model. Specifically, the boundary detecting unit 155 according to the sixth embodiment detects the boundary of the myocardium in the input image by using the corrected boundary pattern model and the boundary model. More specifically, the boundary detecting unit 155 according to the sixth embodiment detects the boundary of the myocardium in the surround of the left ventricle in the input image by using the corrected boundary pattern model and the boundary model.

For example, the boundary detecting unit 155 performs the matching between the brightness pattern in the surround of the boundary when applying the boundary model to the input image while changing in various manners, and the corrected boundary pattern model. Then, the boundary detecting unit 155 detects the boundary of the myocardium in the surround of the left ventricle in the input image by searching the boundary shape in which the brightness pattern which most matched with the corrected boundary pattern model in the boundary shape obtained by changing the boundary model.

First of all, the boundary detecting unit 155 sets "b" described in conjunction with the expression (2) to initially "0", to set the value of the initial energy to infinity (Process 1). Then, the boundary detecting unit 155 creates a shape "x" by the current "b" (Process 2). Then, the boundary detecting unit 155 converts the coordinate system of the created shape "x" into the left ventricle coordinate system of the input image obtained by the process of the coordinate system detecting unit 151 (Process 3).

Then, the boundary detecting unit 155 applies the shape "x" after the coordinate conversion to the input image by using the left ventricle coordinate system of the input image to extract the brightness pattern in the surround of the boundary (Process 4). Then, the boundary detecting unit 155 calculates an error between the extracted brightness pattern and the corrected boundary pattern model (for example, normalization square error) to calculate the current energy (Process 5). Then, the boundary detecting unit 155 determines the magnitude relationship between the current energy and the energy of the previous time (Process 6). The boundary detecting unit 155 terminates the process if the current energy is larger than the energy of the previous time as a result of Process 6.

In contrast, if the current energy is smaller than the energy of the previous time, the boundary detecting unit 155 renews the value of the current "b" (Process 7). In the first time, since the current energy becomes smaller than the initial energy, Process 7 is performed. The boundary detecting unit 155 performs the process from Process 2 to Process 7 repeatedly. Then, if the boundary detecting unit 155 determines that the current energy is larger than the energy of the previous time in Process 6, the "b" provided with the energy of the previous time is obtained as "b" which minimizes the energy.

Figure 34:
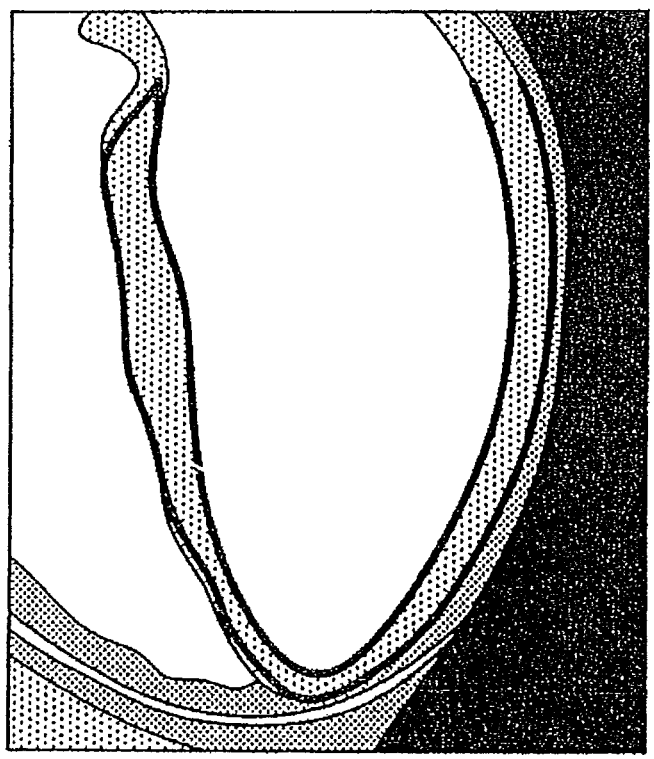
FIG. 34 shows an example of a configuration of a detected example detected by boundary detecting unit according to the sixth embodiment.

Then, the boundary detecting unit 155 detects the shape "x" after the coordinate system conversion created in Process 3 by using the "b" which minimizes the energy, as the boundary of the myocardium in the surround of the left ventricle of the input image. FIG. 34 is a drawing showing an example of detection by the boundary detecting unit according to the sixth embodiment.

For example, the boundary detecting unit 155 according to the sixth embodiment detects the myocardial boundary of the left ventricle in the 4 chamber View as the input image shown in FIG. 34, and displays the same on the display unit 12.

For example, the control unit 15 performs the above-described processes on each of a plurality of the input images along the time series. Then, for example, the control unit 15 obtains a change of a concentration of the contrast agent (the degree of staining) of the myocardium with time by using the boundaries of the myocardia in the peripheries of the left ventricles detected in the respective input images and create a perfusion image which allows analysis of the blood flow state of the myocardium. The control unit 15 stores the result of detection of the myocardial boundary and the perfusion image in the image storage unit 141, and displays the perfusion image on the display unit 12. Alternatively, the control unit 15 may calculate an index value of the heart wall motion such as an ejection fraction (EF) of the left ventricle by using the boundaries of the myocardia in the peripheries of the left ventricles detected in the respective input images.

Referring now to FIG. 35, a process of the medical image processing apparatus 30 according to the sixth embodiment will be described. FIG. 35 is a flowchart showing an example of the process of the medical image processing apparatus 30 according to the sixth embodiment.

As shown in FIG. 35, the medical image processing apparatus 30 according to the sixth embodiment determines whether or not a detection request for the myocardial boundary with respect to the input image is received (Step S101). Here, when the detection request for the myocardial boundary is not received (Negative in Step S101), the medical image processing apparatus 30 waits until the detection request is received.

In contrast, when the detection request is received (Affirmative in Step S101), the coordinate system detecting unit 151 detects the left ventricle coordinate system of the heart in the input image (Step S102), and the regional area detecting unit 152 detects the regional area from the left ventricle coordinate system (Step S103). For example, the coordinate system detecting unit 151 detects the long axis and the short axis of the left ventricle in the input image and the regional area detecting unit 152 detects the left ventricle area, the right ventricle area, and the myocardial area in the input image.

Then, the calculating unit 153 calculates the degree of staining of the regional area (Step S104), and the correcting unit 154 corrects the boundary pattern model by using the degree of staining and creates the corrected boundary pattern model (Step S105). Then, the boundary detecting unit 155 detects the myocardial boundary of the input image from the input image, the corrected boundary pattern model, and the boundary model (Step S106) and terminates the process.

As described above, in the sixth embodiment, the boundary pattern model is corrected according to the degree of staining and the detection of the myocardial boundary in the input image is performed by using the boundary pattern model after the correction. In the related art, the matching between the brightness pattern in the surround of the myocardial boundary of the input image and the boundary pattern model is performed by using the left ventricle coordinate system of the heart in the input image. However, the degrees of staining of the respective regions of the heart in the input image is different depending on the periods elapsed after having injected the contrast agent, or pulsation of the individuals, and the boundary pattern model is not model data covering variations of the degrees of staining as described above. Therefore, in the method of the related art, matching accuracy between the myocardial boundary brightness pattern of the input image and the boundary pattern model may be lowered, and the accuracy of the boundary detection may be lowered.

In contrast, in the sixth embodiment, the correction to cause the boundary pattern model in a regional area to go close to the brightness values of the input image in the corresponding regional area depending on the respective degrees of staining of the corresponding regional area of the input image to be subject to the boundary detection. Then, in the sixth embodiment, the matching with respect to the brightness pattern in the surround of the myocardial boundary of the input image is performed with respect to the corrected boundary pattern model. Accordingly, in the sixth embodiment, improvement of the matching accuracy is achieved by alleviating the effect of the variations in degree of staining by the contrast agent of the input image. Consequently, in the sixth embodiment, improvement of the accuracy of the detection of the myocardial boundary is achieved.

In the above-described description, a case where the corrected boundary pattern model is created depending on the degrees of staining of a respective plurality of the regional areas has been described. However, in the sixth embodiment, a case where the corrected boundary pattern model is created depending on the degree of staining of a single regional area is also applicable.

For example, in the sixth embodiment, a case where the calculating unit 153 calculates the degree of staining of the left ventricle area in the input image specified from the long axis and the correcting unit 154 creates the corrected boundary pattern model by using the degree of staining of the left ventricle area is also applicable. The corrected boundary pattern model in such a case may be data in which the brightness values of the pixels of the left ventricle cavity are corrected on the basis of the degree of staining in the left ventricle area or data in which all the brightness values of the left ventricle cavity, the myocardium, and the outside of the left ventricle are corrected. Also, the sixth embodiment may be a case where the processes by the regional area detecting unit 152, the calculating unit 153, and the correcting unit 154 are performed again by using the result of detection of the boundary detecting unit 155 and redetection of the boundary by the boundary detecting unit 155 is performed by using the recreated corrected boundary pattern model. The number of repetitions of a case where the processes by the regional area detecting unit 152, the calculating unit 153, the correcting unit 154, and the boundary detecting unit 155 are repeated is manually set by the operator, for example, a numerical value, "three times". Alternatively, the processes by the regional area detecting unit 152, the calculating unit 153, the correcting unit 154, and the boundary detecting unit 155 may be repeated until the energy calculated by the boundary detecting unit 155 becomes the minimum.

In the description given above, the case where the boundary pattern model and the boundary model are created from the 4 chamber View group for performing the detection of the myocardial boundary in the surround of the left ventricle in the 4 chamber View described above. However, the sixth embodiment may be a case where the boundary pattern model and the boundary model are created from the 2 chamber View group or the 3 chamber View group for performing the boundary detection of the myocardium in the surround of the left ventricle in the 2 chamber View or the 3 chamber View. A case where the boundary pattern model and the boundary model are created in four cardiac cavities respectively in addition to the left ventricle is also applicable. In such a case, the control unit 15 is capable of detecting the boundary of the myocardium of the right atrium, the boundary of the myocardium of the right ventricle, and the boundary of the myocardium of the left atrium in the input image.

Also, a case where the boundary pattern model and the boundary model are created as three-dimensional information by using the volume data group as the learning image group is also applicable. In such a case, the input image as an object of the boundary detection to be used may be volume data. Also, when the input image as an object of the boundary detection is a cross-sectional image, the control unit 15 is capable of performing the boundary detection by extracting the information of the corresponding cross section from the three-dimensional boundary pattern model and the three-dimensional boundary model.

Also, the sixth embodiment may be a case where the cardiac phase is unified to a diastole phase, for example, even though the cardiac phases in the learning image group are different. Also, the sixth embodiment may be a case where the boundary pattern models and the boundary models are created for the respective cardiac phases by unifying the cardiac phases of the learning image group. Furthermore, the sixth embodiment may be a case where the boundary pattern models and the boundary models are created by classifying into groups by physical characteristics such as ages, sexes, heights, and weights of the tested bodies.

Also, in the sixth embodiment, X-ray images, MRI images, and ultrasonic images may be used as the input images by creating the boundary pattern models and the boundary models by types of the medical images.

Seventh Embodiment

Figure 36:
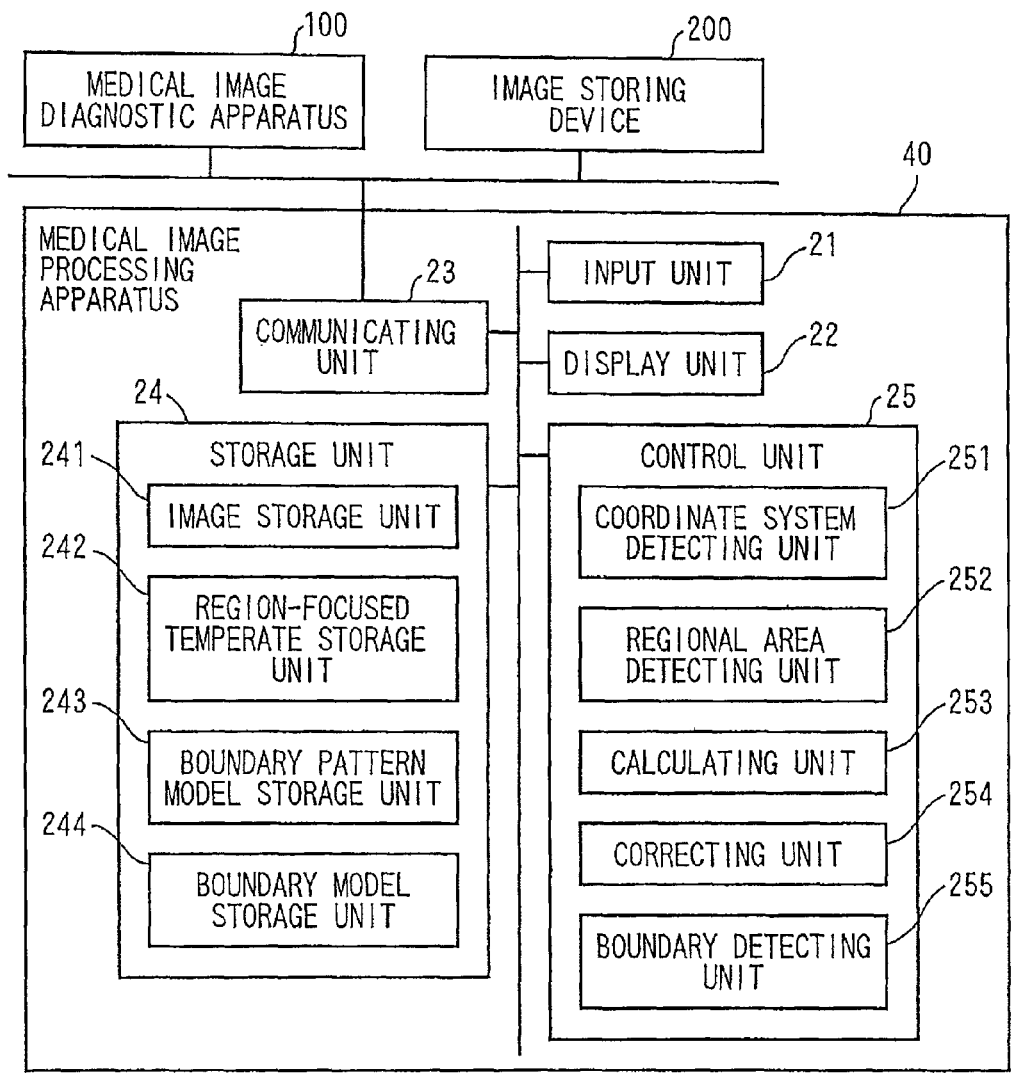
FIG. 36 is a drawing showing an example of the configuration of the medical image processing apparatus according to a seventh embodiment.
Figure 37:
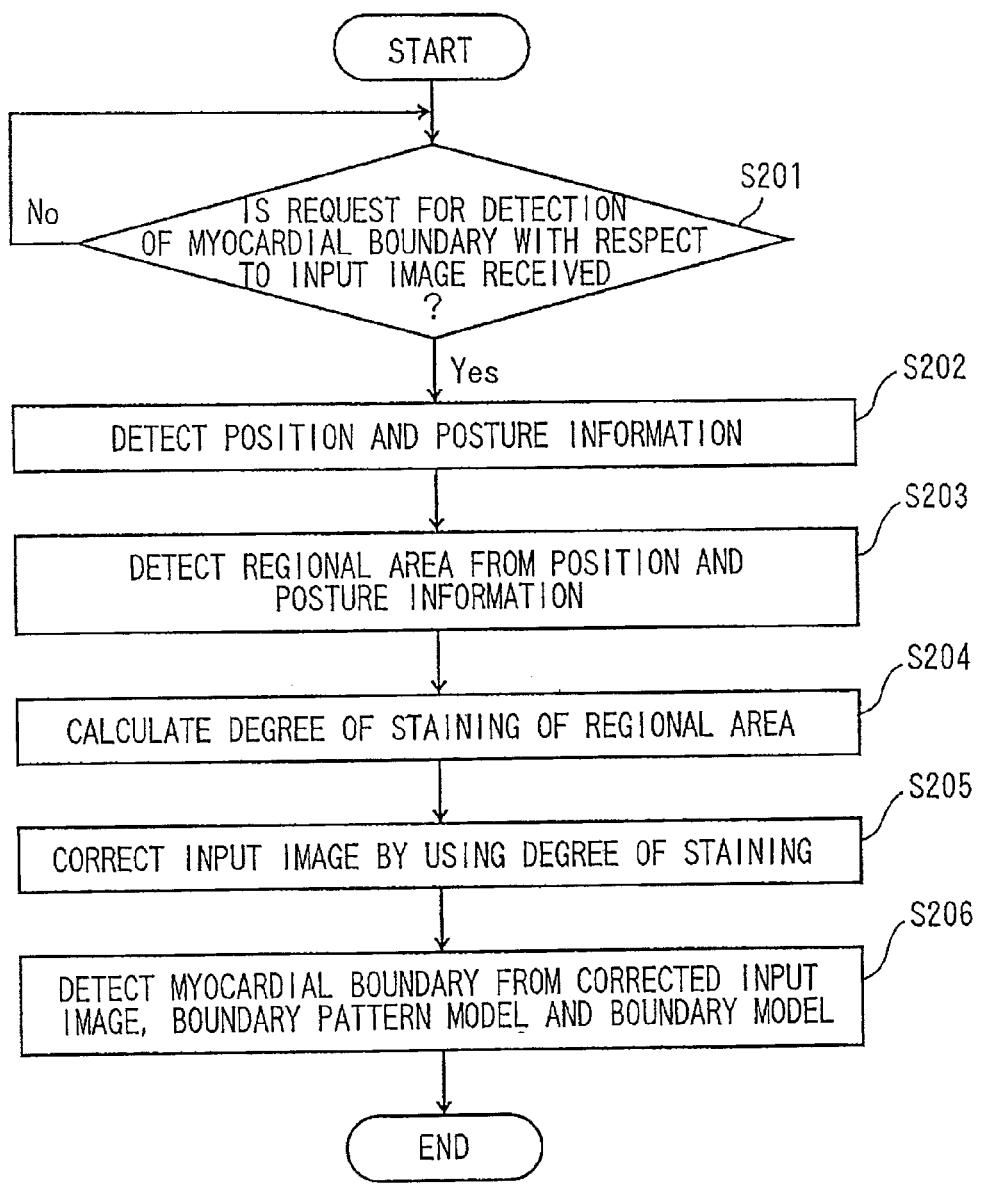
FIG. 37 is a flowchart showing an example of a process of a medical image processing apparatus according to a seventh embodiment.

Referring now to FIG. 36 to FIG. 37, a medical image processing apparatus 40 according to a seventh embodiment will be described.

In the seventh embodiment, a case where a correcting process different from the correcting process described in the sixth embodiment is performed will be described with reference to FIG. 36 and FIG. 37. FIG. 36 shows an example of a configuration of the medical image processing apparatus 40 according to the seventh embodiment.

As illustrated in FIG. 36, the image processing system according to the seventh embodiment includes the medical image diagnostic apparatus 100 and the image storing device 200 in the same manner as the image processing system according to the sixth embodiment described with reference to FIG. 18. Then, as illustrated in FIG. 36, an image processing system according to the seventh embodiment includes the medical image processing apparatus 40 according to the seventh embodiment instead of the medical image processing apparatus 30 according to the sixth embodiment.

The medical image processing apparatus 40 according to the seventh embodiment includes an input unit 21, a display unit 22, a communicating unit 23, a storage unit 24, and a control unit 25 as shown in FIG. 36. Also, the storage unit 24 includes an image storage unit 241, a region-focused temperate storage unit 242, a boundary pattern model storage unit 243, and a boundary model storage unit 244 as shown in FIG. 36. The control unit 25 includes a coordinate system detecting unit 251, a regional area detecting unit 252, a calculating unit 253, a correcting unit 254, and a boundary detecting unit 255 as shown in FIG. 36, and detects the myocardial boundary in the input image by the functions of these processing units.

The input unit 21, the display unit 22, and the communicating unit 23 shown in FIG. 36 have the same functions as the input unit 11, the display unit 12, and the communicating unit 13 described with reference to FIG. 19. The image storage unit 241, the region-focused temperate storage unit 242, the boundary pattern model storage unit 243, and the boundary model storage unit 244 of the storage unit 24 shown in FIG. 36 store similar data to those of the image storage unit 141, the region-focused temperate storage unit 142, the boundary pattern model storage unit 143, and the boundary model storage unit 144 shown in FIG. 19.

The coordinate system detecting unit 251, the regional area detecting unit 252, and the calculating unit 253 of the control unit 25 shown in FIG. 36 perform the same processes as the coordinate system detecting unit 151, the regional area detecting unit 152, and the calculating unit 153 shown in FIG. 19. The input unit 21 also functions as an acquiring unit for acquiring the three-dimensional volume data of the heart.

However, in the seventh embodiment, unlike the correcting unit 154, the correcting unit 254 performs the following correction process. The correcting unit 254 performs the correcting process by using the staining degree with respect to the input image and creates the corrected input image. Specifically, the correcting unit 254 according to the sixth embodiment performs correction for causing the brightness values of the input image of a regional area to go close to the brightness values of the boundary pattern model of the corresponding regional area on the basis of the degree of staining of the corresponding regional area, and creates the corrected input image.

An example of the correcting process performed by the correcting unit 254 in the seventh embodiment will be described. The following are description on the assumption that the brightness value of the "$i^{th}$" pixel is "Ii" of the input image, and the corrected value obtained by correcting "Iij" by the correcting unit 254 is "I'i".

First of all, the correcting unit 254 calculates "a'" as an average value of the brightness values of the pixels of a region corresponding to a region of the input image where the "$i^{th}$" pixel in the pixels of the boundary pattern model is located. Then, the correcting unit 254 acquires a degree of staining "d'" of the region of the input image where the "$i^{th}$" pixel is located from the result of process of the calculating unit 253.

Here, the correcting unit 254 specifies a regional area where a degree of staining closest to "Ii" is calculated among the degrees of staining of the regional areas calculated by the calculating unit 253, for example, to be a region of the input image where the "$i^{th}$" pixel is located.

Then, the correcting unit 254 calculates "I'i" by the following expression (6).

[Expression 6]

$$I'_i = I_i + a' - d' \tag{6}$$

Alternatively, the correcting unit 254 calculates "l'i" by the following expression (7).

[Expression 7]

$$I'_i = I_i \frac{d'}{d'} \quad (7)$$

By performing such a process for all the pixels in the input image, the correcting unit 254 creates a corrected input image.

In the method of correcting the input image described above, a case where the brightness value of the input image is subjected to the rounding process on the basis of the degree of staining is also applicable. Also, the method of correcting the input image is not limited to the arithmetic process on the basis of the expression (6) and the expression (7). As long as the correction to cause the brightness values of the input image to go close to the brightness values of the boundary pattern model is enabled by performing the correcting process by using the degree of staining by a combination of the adding process, the subtracting process, the multiplying process, the dividing process, or the rounding process, the correcting unit 254 may perform an arbitrary arithmetic process.

Then, the boundary detecting unit 255 according to the seventh embodiment detects the boundary of the myocardium in the corrected input image by using the boundary pattern model unlike the boundary detecting unit 155. Specifically, the boundary detecting unit 255 detects the boundary of the myocardium in the corrected input image by using the boundary pattern model and the boundary model.

For example, the boundary detecting unit 255 performs the matching between the brightness pattern in the surround of the boundary when applying the boundary model to the corrected input image while changing the boundary model in various manners, and the boundary pattern model. Then, the boundary detecting unit 255 detects the boundary of the myocardium in the surround of the left ventricle in the corrected input image, that is, the input image by searching the boundary shape in which the brightness pattern which most matched with the boundary pattern model is obtained in the boundary shape whose boundary model is changed.

For reference, description of details of the correcting process performed by the boundary detecting unit 255 is omitted because these are the same as Process 1 to Process 7 performed by the boundary detecting unit 155 described in the sixth embodiment except for by using the corrected input image instead of the input image and by using the boundary pattern model instead of the corrected boundary pattern model.

Referring now to FIG. 37, a process of the medical image processing apparatus 40 according to the seventh embodiment will be described. FIG. 37 is a flowchart showing an example of a process of the medical image processing apparatus 40 according to the seventh embodiment.

As shown in FIG. 37, the medical image processing apparatus 40 according to the seventh embodiment determines whether or not a detection request for the myocardial boundary with respect to the input image is received (Step S201). Here, when the detection request for the myocardial boundary is not received (Negative in Step S201), the medical image processing apparatus 40 waits until the detection request is received.

In contrast, when the detection request is received (Affirmative in Step S201), the coordinate system detecting unit 251 detects the left ventricle coordinate system of the heart in the input image (Step S202), and the regional area detecting unit 252 detects the regional area from the left ventricle coordinate system (Step S203).

Then, the calculating unit 253 calculates the degree of staining in the regional area (Step S204), and the correcting unit 254 corrects the input image by using the degree of staining and creates the corrected input image (Step S205). Then, the boundary detecting unit 255 detects the myocardial boundary of the input image from the corrected input image, the boundary pattern model, and the boundary model (Step S206), and terminates the process.

As described above, in the seventh embodiment, the input image is corrected according to the degree of staining and the boundary detection of the myocardium in the input image is performed by using the input image after the correction as an object of matching of the boundary pattern model. Accordingly, in the seventh embodiment as well, improvement of the matching accuracy is achieved by alleviating the effect of the variations in degree of staining by the contrast agent of the input image. Consequently, in the seventh embodiment, improvement of the accuracy of the detection of the myocardial boundary is achieved.

For reference, the correcting unit 254 may be a case where a region in the input image where the "$i^{th}$" pixel is located is specified from the information of the long axis and the short axis, for example, by using the statistic value described in conjunction with the process of the regional area detecting unit 152 according to the sixth embodiment. In such a case, the correcting unit 254 specifies cardiac cavities or cardiac walls within a predetermined range, and hence creates a corrected input image in which part of the input image is corrected. Therefore, in the seventh embodiment, a case where, for example, the correcting unit 254 enlarges the predetermined range by using the result of detection by the boundary detecting unit 255, creates the corrected input image again, and the boundary detecting unit 255 performs the boundary detection again is also applicable. In such a case, since improvement of accuracy of the detection of the myocardial boundary is achieved, in the seventh embodiment, it is preferable to perform the re-specification of the region and recreation of the corrected input image by the correcting unit 254, and redetection of the boundary by the boundary detecting unit 255 repeatedly by a predetermined number of times.

Also, in the seventh embodiment, even when the specification of the region using the above-described degrees of staining is performed, the specification of the region may be performed on part of pixels to create a corrected input image in which part of the input image is corrected. In such a case as well, improvement of accuracy of detection of the myocardial boundary is achieved by performing the re-specification of the region and the recreation of the corrected input image by the correcting unit 254 and redetect ion of the boundary by the boundary detecting unit 255.

Also, in the seventh embodiment, the contents as described in the sixth embodiment may be applied except for a point "the object to be corrected is the input image, and the boundary detection is performed by using the corrected input image and the boundary pattern model"

As described above, in the sixth embodiment and the seventh embodiment, the correction is performed so that the value of the predetermined regional area of the boundary pattern model goes close to that of the input image, and the boundary detection of the myocardium is performed by using the data after correction.

Incidentally, in the sixth embodiment and the seventh embodiment described above, the case where the boundary detection of the myocardium is performed by using the boundary pattern model and the boundary model has been described. However, the sixth embodiment and the seventh embodiment may be a case where the boundary detection of the myocardium is performed without by using the boundary model.

Here, the boundary pattern model is information in which a plurality of brightness value rows of pixels to which information of regions of the heart are indexed are arranged, as described above. Also, in the boundary pattern model, spatial information of the heart is included in the order of arrangement of the pixels in the brightness value rows and the order of arrangement of the brightness value rows. Therefore, in the sixth embodiment, the boundary detecting unit 155 is capable of detecting the boundary of the myocardium by performing matching the corrected boundary pattern models and the input images in a round-robin system, for example, while varying the distance between the pixels in the corrected boundary pattern model under the condition limited by the spatial information of the heart in the left ventricle coordinate system and the corrected boundary pattern model.

Also, in the seventh embodiment, the boundary detecting unit 255 is capable of detecting the boundary of the myocardium by performing matching the boundary pattern models and the corrected input images in a round-robin system, for example, while varying the distance between the pixels in the corrected boundary pattern model under the condition limited by the spatial information of the heart in the left ventricle coordinate system and the boundary pattern model.

A case where the image processing methods described in the sixth embodiment and the seventh embodiment described above are executed by the medical image diagnostic apparatus 100 is also applicable.

Also, the image processing programs executed by the medical image processing apparatus 30 in the sixth embodiment and the medical image processing apparatus 40 in the seventh embodiment are provided by being integrated in a ROM or the like in advance.

The image processing program executed by the medical image processing apparatus 30 in the sixth embodiment and the medical image processing apparatus 40 in the seventh embodiment may be configured to be provided by being recorded in a computer readable recording medium such as a CD-ROM, a flexible disk (FD), a CD-R, a DVD (digital Versatile Disk) file in an installable format or in an executable format.

Furthermore, the image processing program to be executed by the medical image processing apparatus 30 in the sixth embodiment and the medical image processing apparatus 40 in the seventh embodiment may be configured to be stored in a computer connected to a network such as internet and downloaded via the network. Furthermore, the image processing program to be executed by the medical image processing apparatus 30 in the sixth embodiment and the medical image processing apparatus 40 in the seventh embodiment may be configured to be provided or distributed via the network such as internet.

The image processing program to be executed by the medical image processing apparatus 30 in the sixth embodiment and the medical image processing apparatus 40 in the seventh embodiment have a module configuration including the above-described respective units (the coordinate system detecting unit, the regional area detecting unit, the calculating unit, the correcting unit, and the boundary detecting unit), and as an actual hardware, the above-described respective units are loaded on a main storage device by the CPU reading out the image processing program from the above-described ROM and executing the same, so that the coordinate system detecting unit, the regional area detecting unit, the calculating unit, the correcting unit, and the boundary detecting unit are created on the main storage device.

As described above, according to the sixth embodiment and the seventh embodiment, improvement of accuracy of detection of the myocardial boundary is achieved.

Modifications

For reference, the medical image processing apparatuses 10, 20, 30, 40 in the above-described respective embodiments may be realized by using a general-purpose computer as basic hardware, for example. In other words, the acquiring unit, the coordinate system detecting unit, the regional area detecting unit, the calculating unit, the correcting unit, the boundary detecting unit, and the displaying unit may be realized by causing a processor mounted on the above-described computer to execute a program. At this time, the medical image processing apparatuses 10, 20, 30, 40 may be realized by installing the above-described program in the computer in advance, or may be realized by storing the same in a storage medium such as a CD-ROM or by distributing the above-described program via the network and installing the program in the computer as needed. Also, the acquiring unit, the coordinate system detecting unit, and the boundary detecting unit may be realized by using the storage medium such as a memory or a hard disk integrated into or externally connected to the above-described computer, or a CD-R, a CD-RW, a DVD-RAM, and a DVD-R as needed.

The present invention is not limited to the embodiments described above as is, and components may be modified and embodied without departing from the scope of the invention in the stage of implementation. Various modes of the invention are achieved by combining the plurality of components disclosed in the embodiments described above as needed. For example, several components may be eliminated from all the components shown in the embodiment. In addition, the components in different embodiments may be combined as needed.

REFERENCE SIGNS LIST

10, 20, 20, 40 . . . medical image processing apparatus, 101 . . . acquiring unit, 102 . . . coordinate system detecting unit, 103 . . . boundary detecting unit, 104 . . . display unit, 110 . . . storage unit

The invention claimed is:

1. A medical image processing apparatus comprising:
an acquiring unit configured to acquire volume data of a heart;
a coordinate system detecting unit configured to detect a three-dimensional left ventricle coordinate system composed of three axes including at least a left ventricle long axis of the heart from the volume data;
a boundary detecting unit configured to use a boundary model expressed in the left ventricle coordinate system to detect a left ventricle boundary from the volume data by deforming the boundary model so that an error between a boundary pattern obtained by applying the boundary model to the volume data and a predetermined boundary pattern model becomes small; and
a display monitor configured to display the detected left ventricle boundary on a cross-sectional image of the heart, the cross-sectional image being orthogonal to at least one axis of the three axes of the left ventricle coordinate system, wherein the boundary pattern model is obtained by modeling a pattern of brightness values in a myocardium and a surround of the myocardial boundary in an image enhanced by a contrast agent by learning, the apparatus further comprises:

a calculating unit configured to calculate a degree of staining indicating a concentration of the contrast agent of a predetermined regional area in the volume data on the basis of the left ventricle coordinate system, and a correcting unit configured to use a degree of staining of the regional area to perform a correction to cause brightness values of the volume data and brightness values of the boundary pattern model to go close to each other in the corresponding regional area, and the boundary detecting unit detects a myocardial boundary in the volume data by using the data after the correction by the correcting unit.

2. The medical image processing apparatus according to claim 1, wherein the coordinate system detecting unit detects any one of axes which set a 4 chamber view, a 3 chamber view, or a 2 chamber view of the heart from the volume data as an axis of the left ventricle coordinate system in addition to the left ventricle long axis.

3. The medical image processing apparatus according to claim 1, wherein the coordinate system detecting unit detects the left ventricle coordinate system in which directions of the three axes are orthogonal to each other and an original point thereof is located at a position of a center of a left ventricle of the heart from the volume data.

4. The medical image processing apparatus according to claim 1, wherein the coordinate system detecting unit detects the left ventricle coordinate system by performing matching between the volume data and a left ventricle cross-sectional image pattern created in advance.

5. The medical image processing apparatus according to claim 1, wherein the coordinate system detecting unit performs matching between the volume data with an image pattern in a surround of a position of a cardiac apex learned in advance and an image pattern in a surround of a position of a mitral valve to obtain the position of the cardiac apex and the position of the mitral valve of the heart respectively, and detects the left ventricle long axis from the position of the cardiac apex and the position of the mitral valve.

6. The medical image processing apparatus according to claim 5, wherein the coordinate system detecting unit detects the left ventricle coordinate system by using any one of a position of a right ventricle corner point, a position of a tricuspid valve, and a position of a left ventricle outflow tract of the heart after the detection of the left ventricle long axis.

7. The medical image processing apparatus according to claim 1, wherein the coordinate system detecting unit notifies a user the fact that the detection is not possible when the left ventricle coordinate system cannot be detected on the display monitor.

8. The medical image processing apparatus according to claim 1, wherein the display monitor displays the volume data on the basis of the coordinate system of the volume data when the coordinate system detecting unit cannot detect the left ventricle coordinate system.

9. The medical image processing apparatus according to claim 1, further comprising:

an evaluating unit configured to evaluate an error between the predetermined boundary pattern model and the boundary pattern relating to the detected left ventricle boundary, wherein the display monitor displays a result of evaluation of the error evaluated by the evaluating unit.

10. The medical image processing apparatus according to claim 9, wherein the evaluating unit evaluates whether or not the error is smaller than a threshold value.

11. The medical image processing apparatus according to claim 10, wherein when the error is smaller than the threshold value in the evaluating unit, the display monitor displays the left ventricle boundary on the cross-sectional image together with the cross-sectional image.

12. The medical image processing apparatus according to claim 10, wherein when the error is larger than the threshold value in the evaluating unit, the display monitor displays the fact that the left ventricle boundary cannot be detected.

13. The medical image processing apparatus according to claim 10, wherein when the error is larger than the threshold value in the evaluating unit, the display monitor displays the volume data except for the left ventricle boundary.

14. The medical image processing apparatus according to claim 10, wherein when the error is larger than the threshold value in the evaluating unit, the coordinate system detecting unit detects the left ventricle coordinate system again under predetermined different conditions.

15. The medical image processing apparatus according to claim 10, wherein when the error is larger than the threshold value in the evaluating unit, the apparatus is configured to receive the left ventricle coordinate system with respect to the coordinate system detecting unit.

16. The medical image processing apparatus according to claim 1, wherein the boundary model is a boundary model including a myocardial inner boundary and a myocardial outer boundary of the left ventricle combined with each other.

17. The medical image processing apparatus according to claim 1, wherein the boundary model is a boundary model on the inner side of the myocardium of the left ventricle or a boundary model on the outside of the myocardium thereof.

18. The medical image processing apparatus according to claim 1, wherein the volume data is volume data imaged by a CT apparatus or an MR apparatus.

19. The medical image processing apparatus according to claim 1, further comprising a regional area detecting unit configured to detect the regional area in the volume data by using the left ventricle coordinate system, wherein the calculating unit performs a staining degree calculating process by using the regional area detected by the regional area detecting unit.

20. The medical image processing apparatus according to claim 1 wherein the correcting unit performs a correcting process by using the degree of staining on the boundary pattern model and creates a corrected boundary pattern model, and the boundary detecting unit detects the boundary of the myocardium in the volume data by using the corrected boundary pattern model.

21. The medical image processing apparatus according to claim 1, wherein the correcting unit performs a correcting process by using the degree of staining on the volume data and creates the corrected volume data, and the boundary detecting unit detects the boundary of the myocardium in the corrected volume data by using the boundary pattern model.

22. The medical image processing apparatus according to claim 1, wherein the correcting unit performs the correcting process by using the degree of staining by a combination of an adding process, a subtracting process, a multiplying process, a dividing process, or a rounding process.

23. The medical image processing apparatus according to claim 1, wherein the calculating unit calculates a statistic representative value in the brightness value row of a plurality of pixels which constitute the regional area as a staining degree of the corresponding regional area.

24. The medical image processing apparatus according to claim 19, wherein the regional area detecting unit detects a plurality of the regional areas as the predetermined regional area, and
the calculating unit calculates the degrees of staining of the respective plurality of regional areas.

25. The medical image processing apparatus according to claim 19, wherein the regional area detecting unit detects an area including at least one of the ventricles, atriums, a left ventricle outflow tract, a valve ring, a papillary muscle, the myocardium, and a coronary artery as the predetermined regional area.

26. The medical image processing apparatus according to claim 19, wherein the regional area detecting unit detects a predetermined range determined by a long axis included in the left ventricle coordinate system as the regional area in the volume data.

27. The medical image processing apparatus according to claim 19, wherein the coordinate system detecting unit further detects a short axis of the heart in the volume data as the left ventricle coordinate system, and
the regional area detecting unit detects a predetermined range determined by the direction of the long axis and the direction of the short axis as the regional area in the volume data.

28. A medical image processing method comprising:
acquiring volume data of a heart;
detecting a three-dimensional left ventricle coordinate system composed of three axes including at least a left ventricle long axis of the heart from the volume data;
using a boundary model expressed in the left ventricle coordinate system to deform the boundary model so that an error between a boundary pattern obtained by applying the boundary model to the volume data and a predetermined boundary pattern model becomes small, thereby detecting a left ventricle boundary from the volume data;
displaying the detected left ventricle boundary on a cross-sectional image, the cross-sectional image being orthogonal to at least one axis of the three axes of the left ventricle coordinate system;
obtaining the boundary pattern model by modeling a pattern of brightness values in a myocardium and a surround of the myocardial boundary in an image enhanced by a contrast agent by learning;
calculating a degree of staining indicating a concentration of the contrast agent of a predetermined regional area in the volume data on the basis of the left ventricle coordinate system;
using a degree of staining of the regional area to perform a correction to cause brightness values of the volume data and brightness values of the boundary pattern model to go close to each other in the corresponding regional area; and
detecting a myocardial boundary in the volume data by using the data after the correction.

29. A medical image processing apparatus comprising:
a computer;
a memory connected to the computer storing a program, a boundary pattern model and a boundary model; and
a monitor,
wherein the computer, when executing the program, is configured to perform the following operations:
acquiring volume data of a heart;
detecting a three-dimensional left ventricle coordinate system composed of three axes including at least a left ventricle long axis of the heart from the volume data;
using the boundary model expressed in the left ventricle coordinate system to deform the boundary model so that an error between a boundary pattern obtained by applying the boundary model to the volume data and the boundary pattern model becomes small, thereby detecting a left ventricle boundary from the volume data;
displaying on the monitor the detected left ventricle boundary on a cross-sectional image, the cross-sectional image being orthogonal to at least one axis of the three axes of the left ventricle coordinate system;
obtaining the boundary pattern model by modeling a pattern of brightness values in a myocardium and a surround of the myocardial boundary in an image enhanced by a contrast agent by learning;
calculating unit a degree of staining indicating a concentration of the contrast agent of a predetermined regional area in the volume data on the basis of the left ventricle coordinate system;
using a degree of staining of the regional area to perform a correction to cause brightness values of the volume data and brightness values of the boundary pattern model to go close to each other in the corresponding regional area; and
detecting a myocardial boundary in the volume data by using the data after the correction.

* * * * *